United States Patent
Murakami

(10) Patent No.: US 12,013,319 B2
(45) Date of Patent: Jun. 18, 2024

(54) SAMPLE PRODUCING METHOD

(71) Applicant: HIRATA CORPORATION, Kumamoto (JP)

(72) Inventor: Seigo Murakami, Kumamoto (JP)

(73) Assignee: HIRATA CORPORATION, Kumamoto (JP)

( * ) Notice: Subject to any disclaimer, the term of this patent is extended or adjusted under 35 U.S.C. 154(b) by 425 days.

(21) Appl. No.: 17/358,444

(22) Filed: Jun. 25, 2021

(65) Prior Publication Data

US 2021/0318210 A1 Oct. 14, 2021

Related U.S. Application Data

(63) Continuation of application No. PCT/JP2019/004647, filed on Feb. 8, 2019.

(51) Int. Cl.
*G01N 1/30* (2006.01)
*G01N 33/483* (2006.01)
*G02B 21/34* (2006.01)

(52) U.S. Cl.
CPC ............ *G01N 1/30* (2013.01); *G01N 33/4833* (2013.01); *G02B 21/34* (2013.01)

(58) Field of Classification Search
CPC .... G01N 1/30; G01N 33/4833; G01N 1/2813; G02B 21/34
See application file for complete search history.

(56) References Cited

U.S. PATENT DOCUMENTS

| | | | |
|---|---|---|---|
| 6,302,985 B1 | 10/2001 | Takahashi et al. | |
| 6,474,386 B2 | 11/2002 | Takahashi et al. | |
| 7,799,309 B2 | 9/2010 | Reynolds et al. | |
| 10,184,862 B2 | 1/2019 | Beer | |
| 10,429,280 B2 | 10/2019 | Beer | |
| 2002/0029840 A1 | 3/2002 | Takahashi et al. | |
| 2002/0093121 A1 | 7/2002 | Greinke | |
| 2005/0232845 A1 | 10/2005 | Reynolds et al. | |

(Continued)

FOREIGN PATENT DOCUMENTS

| | | |
|---|---|---|
| JP | H10232192 A | 9/1998 |
| JP | 2007057255 A | 3/2007 |

(Continued)

OTHER PUBLICATIONS

Office Action issued on Jul. 11, 2023, in corresponding Chinese Patent Application No. 201980090830.9 and English translation of the Office Action. (15 pages).

(Continued)

*Primary Examiner* — Peter J Macchiarolo
*Assistant Examiner* — John M Royston
(74) *Attorney, Agent, or Firm* — BUCHANAN INGERSOLL & ROONEY PC

(57) ABSTRACT

A sample producing method of producing an observation sample by placing an observation target object on an optically transparent plate, comprising a placement step of placing the observation target object on a surface of a liquid pool retained on the plate, and a fixing step of making an amount of a liquid of the liquid pool on the plate larger on one end portion side of the plate than on the other end portion side and attaching and fixing the observation target object to a surface of the plate sequentially from the other end portion toward the one end portion.

9 Claims, 22 Drawing Sheets

(56) References Cited

U.S. PATENT DOCUMENTS

| | | |
|---|---|---|
| 2009/0117611 A1 | 5/2009 | Becker et al. |
| 2011/0215081 A1 | 9/2011 | Beer |
| 2011/0305842 A1* | 12/2011 | Kram .................. G02B 21/34 |
| | | 118/58 |
| 2014/0287456 A1 | 9/2014 | Angros |
| 2015/0008096 A1 | 1/2015 | Ito |
| 2018/0321116 A1 | 11/2018 | Beer |
| 2018/0348100 A1 | 12/2018 | Beer |
| 2020/0088614 A1 | 3/2020 | Beer |

FOREIGN PATENT DOCUMENTS

| | | |
|---|---|---|
| JP | 2008151657 A | 7/2008 |
| JP | 2008151755 A | 7/2008 |
| JP | 2012508888 A | 4/2012 |
| JP | 2013160718 A | 8/2013 |
| JP | 2016176842 A | 10/2016 |
| WO | 2010056883 A1 | 5/2010 |
| WO | 2019017291 A1 | 1/2019 |

OTHER PUBLICATIONS

International Search Report (PCT/ISA/210) with translation and Written Opinion (PCT/ISA/237) mailed on Apr. 16, 2019, by the Japan Patent Office as the International Searching Authority for International Application No. PCT/JP2019/004647.

The Extended European Search Report issued on Oct. 22, 2021, by the European Patent Office in corresponding European Patent Application No. 19914437.9. (7 pages).

Office Action dated Mar. 22, 2022, issued in corresponding Japanese Patent Application No. 2020-570320, 8 pages including 6 pages of English Translation.

* cited by examiner

F I G. 2D
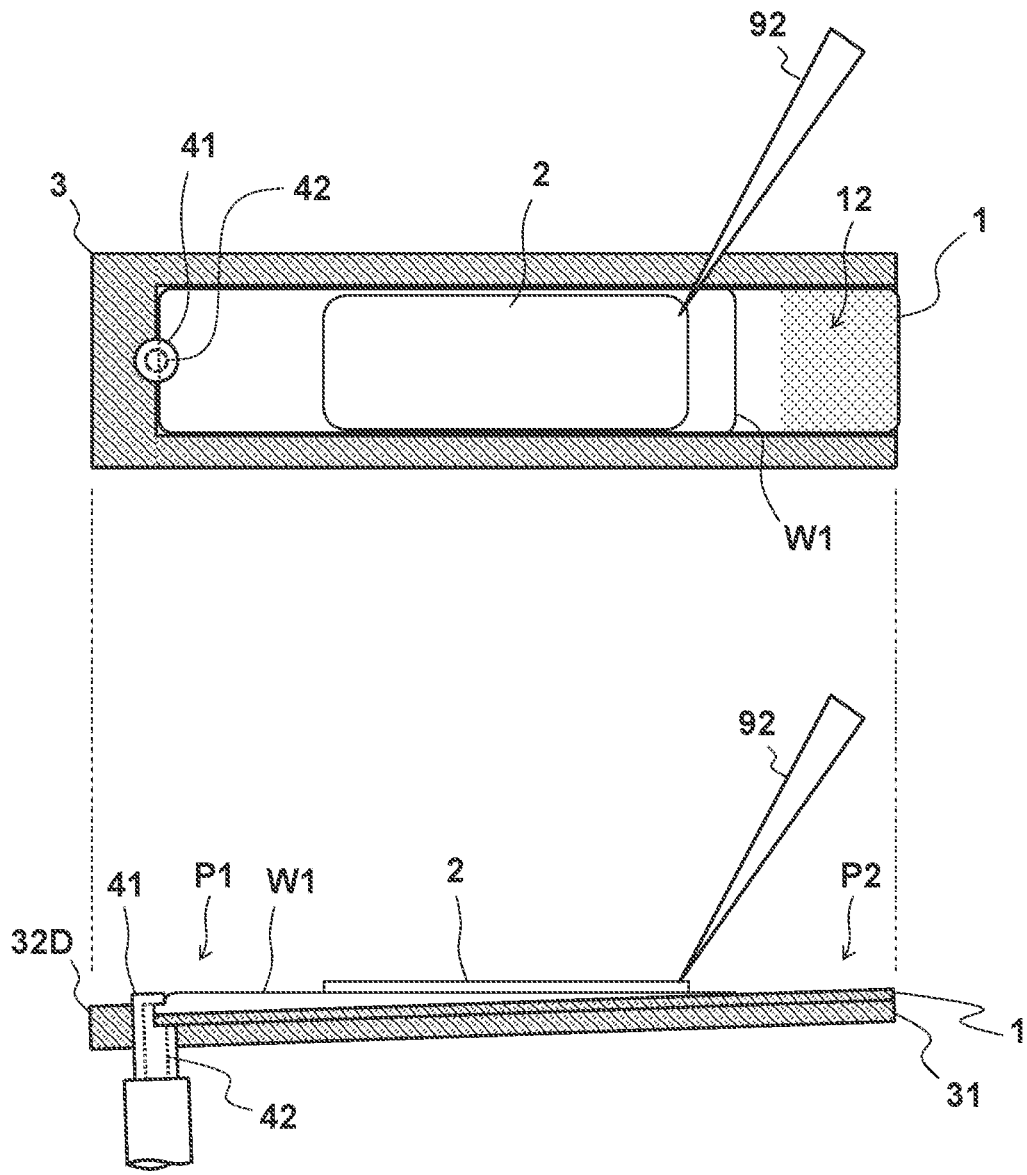

SAMPLE PRODUCING METHOD

CROSS-REFERENCE TO RELATED APPLICATION(S)

This application is a continuation of International Patent Application No. PCT/JP2019/004647 filed on Feb. 8, 2019, which claims priority to, the entire disclosures of which is incorporated herein by reference.

TECHNICAL FIELD

The present invention relates to a sample producing method.

BACKGROUND ART

An observation sample used in a microscope observation or the like is generally produced by placing an observation target object such as a tissue piece on an optically transparent plate that is also called a microscope slide (see PTL 1). For example, a liquid such as water is retained on a plate to form a liquid pool, and after that, an observation target object is placed on the liquid pool, thereby producing an observation sample.

CITATION LIST

Patent Literature

PTL 1: Japanese Patent Laid-Open No. 2008-151657

SUMMARY OF INVENTION

Technical Problem

The liquid pool may move the observation target object by its flow. For this reason, after the observation target object is placed on the liquid pool when producing the observation sample, the observation target object needs to be appropriately fixed to the plate surface.

It is an exemplary object of the present invention to reliably and easily produce an observation sample.

Solution to Problem

One aspect of the present invention is related to a sample producing method, and the sample producing method a sample producing method of producing an observation sample by placing an observation target object on an optically transparent plate, comprising a placement step of placing the observation target object on a surface of a liquid pool retained on the plate, and a fixing step of making an amount of a liquid of the liquid pool on the plate larger on one end portion side of the plate than on the other end portion side and attaching and fixing the observation target object to a surface of the plate sequentially from the other end portion toward the one end portion.

Advantageous Effects of Invention

According to the present invention, it is possible to reliably and easily produce an observation sample.

BRIEF DESCRIPTION OF DRAWINGS

FIG. 2D shows a schematic top view and a schematic sectional view for explaining a step of the sample producing method;

DESCRIPTION OF EMBODIMENTS

Figure 1A:
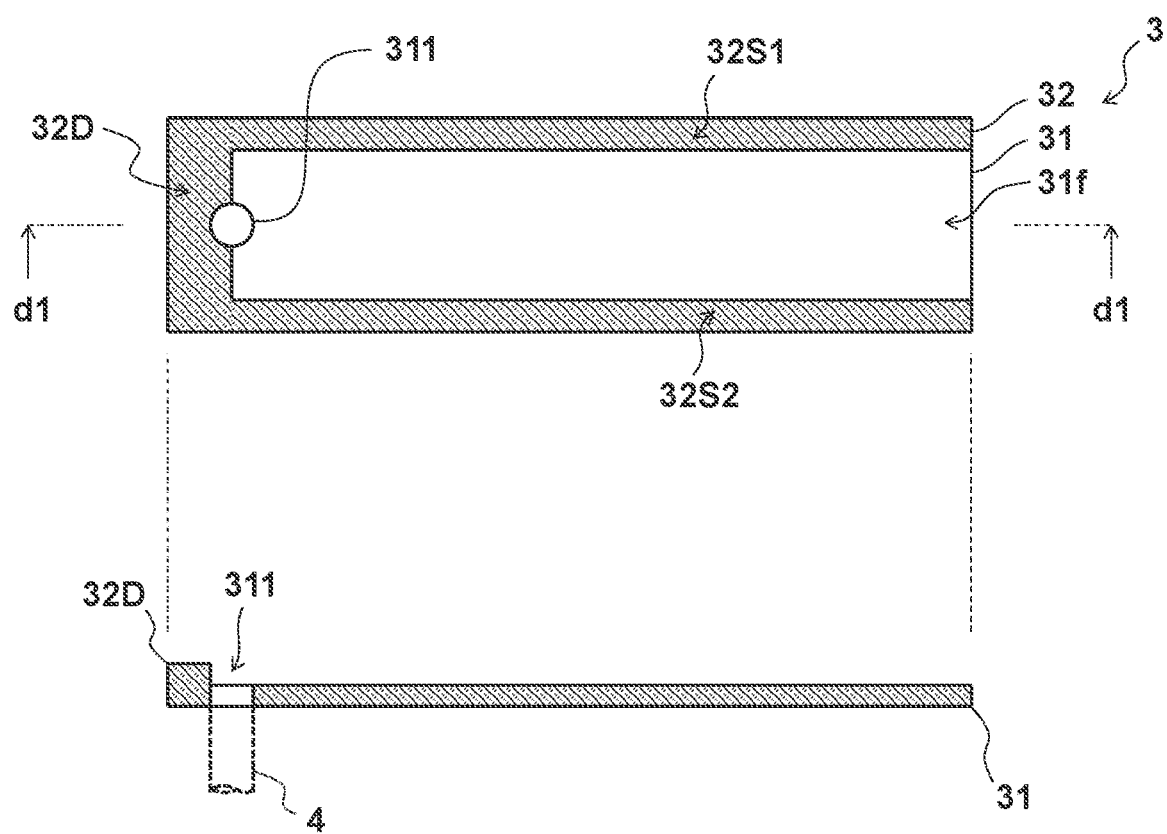
FIG. 1A shows a schematic top view and a schematic sectional view of the configuration of a base plate.

Hereinafter, embodiments will be described in detail with reference to the accompanying drawings. It should be noted that the following embodiments are not intended to limit the scope of the appended claims, and that not all the combinations of features described in the embodiments are necessarily essential to the present invention. Of a plurality of features described in the embodiments, two or more features may arbitrarily be combined. In addition, the same reference numerals denote the same or similar parts, and a repetitive description will be omitted.

First Embodiment

FIG. 1A shows, side by side, a top view (plan view) showing the configuration of a base plate 3 that is one of tools used in a sample producing method according to the first embodiment and a sectional view taken along a line d1-d1 in the top view (to be simply referred to as a "sectional view" hereinafter, and this also applies to the remaining sectional views in this embodiment). The base plate 3 includes a support portion 31 and a frame portion 32. The support portion 31 substantially has a rectangular shape in the top view, and a hole 311 is provided at one end portion. As will be described later in detail, a liquid discharge mechanism 4 configured to discharge a liquid can be installed in the hole 311, as shown in FIG. 1A, and a liquid on the support portion 31 can thus be discharged.

The frame portion 32 is a U-shaped wall body provided from the upper surface of the support portion 31 to surround three sides of the base plate 3, and the support portion 31 and the frame portion 32 are integrally provided. The frame portion 32 includes an edge portion 32D located on the side on one end portion side (the left side in FIG. 1A) in the longitudinal direction (the left-and-right direction in FIG. 1A) of the support portion 31, and edge portions 32S1 and 32S2 extending from the edge portion 32D and facing each other. No wall body exists on the other end portion side (the right side in FIG. 1A) in the longitudinal direction of the support portion 31, and the frame portion 32 is open in this portion. The hole 311 extending through the base plate 3 is provided at the boundary between the edge portion 32D and the support portion 31. The hole 311 is preferably provided at the intermediate position of the edge portion 32D in the widthwise direction (the up-and-down direction in FIG. 1A) of the base plate 3.

As described above, in the base plate 3, a portion surrounded by the U-shaped frame portion 32 is a placement surface 31f. In other words, in the placement surface 31f, three sides formed by the edge portions 32D, 32S1, and 32S2 are closed by the frame portion 32, and one remaining portion faces the outside of the base plate 3. Note that in this embodiment, the frame portion 32 and the support portion 31 are integrally formed. As another embodiment, at least a part of the frame portion 32 may be formed as a member separated from the support portion 31. The separate member may be configured to be detachable from the support portion 31.

As will be described later in detail, at least the surface of the frame portion 32 can made of a material (a lyophobic or liquid-repellent material) that hardly fits to a predetermined liquid. In this embodiment, the surface of the frame portion 32 is treated (for example, coating) by a material having a lyophobic property. For example, if water is used as the liquid, coating using a silicon resin or fluororesin is performed for the frame portion 32 to obtain a hydrophobic property or water-repellency. The above-described edge portions 32D, 32S1, and 32S2 can also be expressed as lyophobic portions 32D, 32S1, and 32S2. Note that the entire base plate 3 including the frame portion 32 may be made of a material having a lyophobic property, and the placement surface 31f may be coated with a material having a lyophilic property.

Note that the lyophobic property is a relative property representing a characteristic to a liquid on a certain upper surface, and can typically be decided based on whether the contact angle of a liquid droplet on the upper surface satisfies a predetermined condition. For example, let Ow be the contact angle of a liquid droplet. For example, if $45°<Ow$, preferably, $60°<Ow$ is satisfied, it may be decided that a surface has a lyophobic property.

With this configuration, the base plate 3 can arrange a predetermined plate (to be described later) and can also be expressed as a placement table, a setting table, a support table, a sample producing jig, or the like.

Figure 1B:
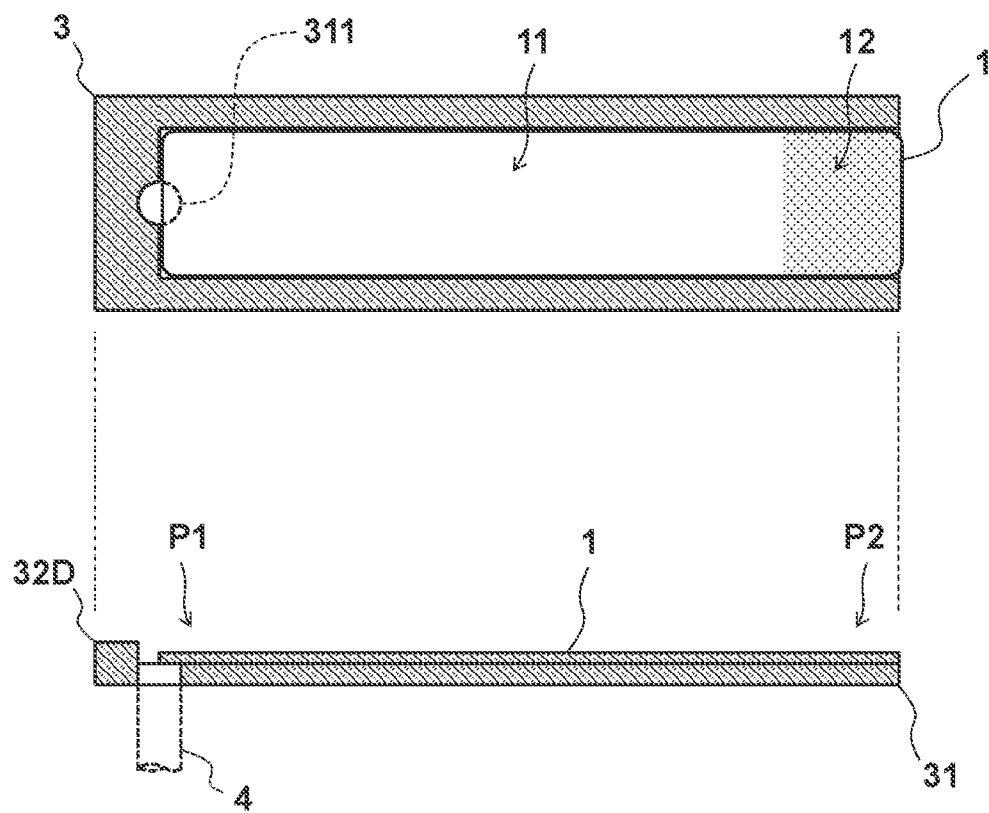
FIG. 1B shows a schematic top view and a schematic sectional view of a configuration in which a plate is placed on the base plate.

FIG. 1B shows a top view and a sectional view showing a mode in which a plate 1 is arranged on the placement surface 31f in the support portion 31 of the base plate 3. The plate 1 substantially has a rectangular shape in the top view and is made of an optically transparent material such as glass. As will be described later in detail, an observation target object that is an observation target is placed on the plate 1, thereby producing a predetermined observation sample. In this embodiment, the plate 1 includes a placement portion 11 configured to place the observation target object, and a frosted portion 12 on which predetermined information such as identification information can be printed.

Note that the observation target object is typically a slice of a tissue piece that is cut out by solidifying a tissue piece taken from a subject such as a patient by paraffin or the like and slicing the solidified tissue block. The plate 1 can also be expressed as a microscope slide, or a sample plate, an observation target object placement plate, an optical observation plate, or the like.

To facilitate the explanation, as shown in FIG. 1B, one end portion of the base plate 3 on the side where the liquid discharge mechanism 4 is provided will be defined as a portion P1, and the other end portion on the opposite side will be defined as a portion P2. In other words, the portion P1 is an end portion (liquid discharge downstream-side end portion) on the downstream side of the direction in which a liquid flows at the time of liquid discharge (to be described later), and the portion P2 is an end portion (liquid discharge upstream-side end portion) on the upstream side of the direction in which a liquid flows at the time of liquid discharge.

FIGS. 2A to 2F show steps of a sample producing method according to this embodiment. This method is roughly divided into a step of arranging the plate 1 on the base plate 3, a step of forming a liquid pool on the plate 1, a step of placing an observation target object on the liquid pool, and a step of fixing the observation target object to the plate 1 while removing the liquid pool.

Figure 2A:
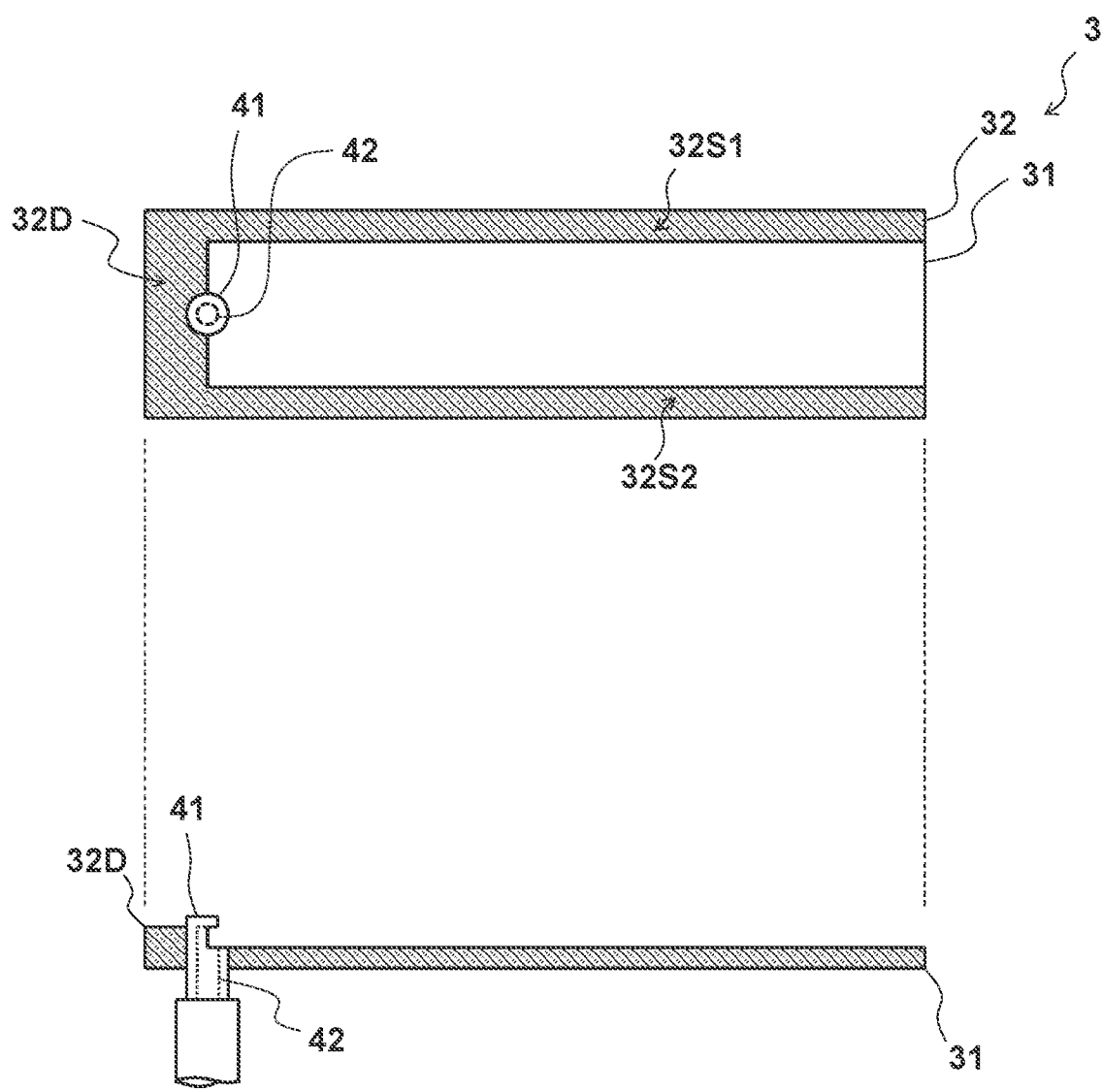
FIG. 2A shows a schematic top view and a schematic sectional view for explaining a step of a sample producing method.

FIG. 2A shows a top view and a sectional view showing a step of preparing the base plate 3. In the step shown FIG. 2A, a suction nozzle 41 is installed as the liquid discharge mechanism 4 in the base plate 3. When a suction driving mechanism (not shown) provided in the suction nozzle 41 operates, the liquid of a liquid pool formed later is sucked and discharged via a channel 42, and the suction nozzle 41 can thus remove the liquid pool. Note that the suction driving mechanism of the suction nozzle 41 is configured to start the operation at a desired timing in accordance with an operation input by a user (an operator who produces a sample) and thus start suction of the liquid via the suction nozzle 41.

Note that if the support portion 31 and the frame portion 32 are formed as separate members, in this step, the frame portion 32 is arranged as an external lyophobic plate member on the support portion 31 before or after the installation of the suction nozzle 41.

Figure 2B:
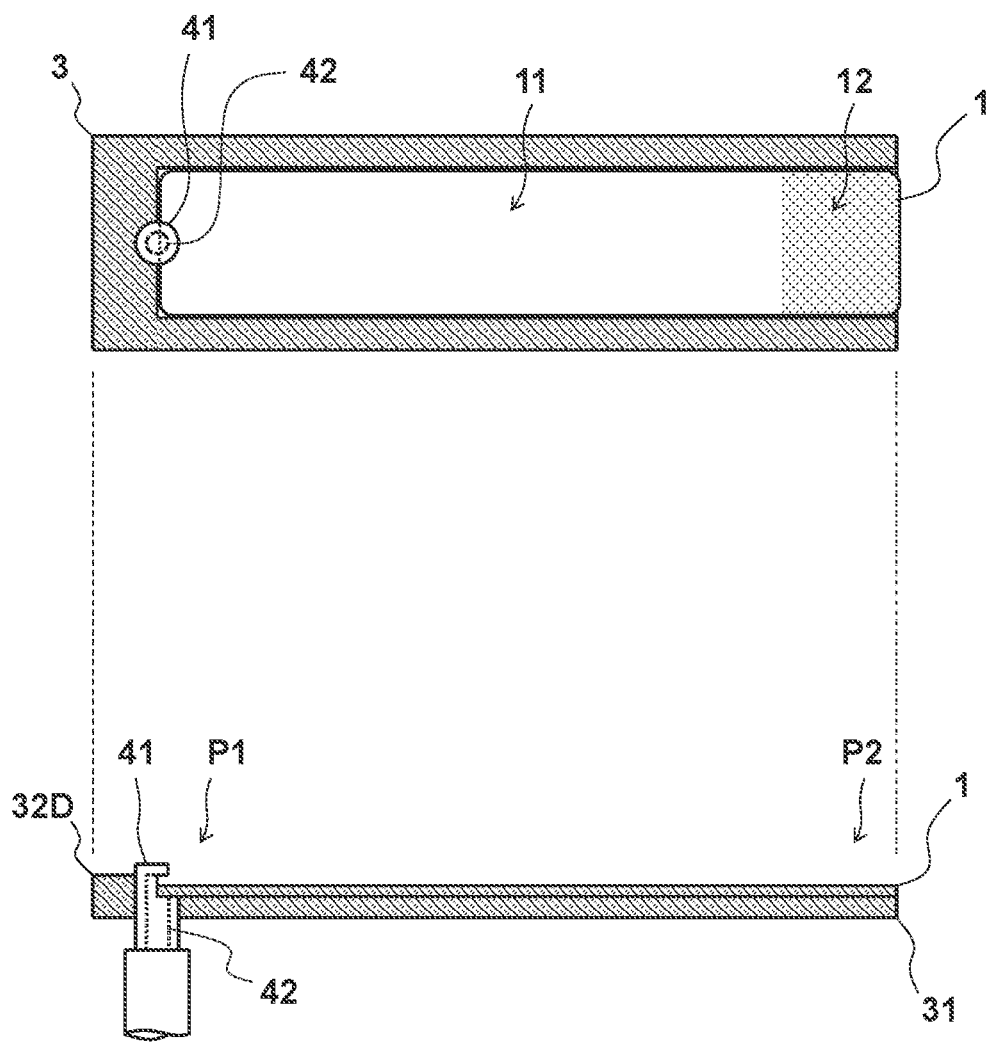
FIG. 2B shows a schematic top view and a schematic sectional view for explaining a step of the sample producing method.

FIG. 2B shows a top view and a sectional view showing a step of arranging the plate 1 on the base plate 3 prepared in the step shown in FIG. 2A. The plate 1 is placed on the placement surface 31f and slid until the portion P1 comes close to the edge portion 32D, thereby completing setting of the plate 1 on the base plate 3. At this time, since the channel 42 communicates with the space on the plate 1, the suction nozzle 41 can suck the liquid of a liquid pool formed later and remove the liquid pool. Note that the plate 1 is arranged here such that the frosted portion 12 is located on the liquid discharge upstream side. However, the frosted portion 12 may be located on the liquid discharge downstream side.

Figure 2C:
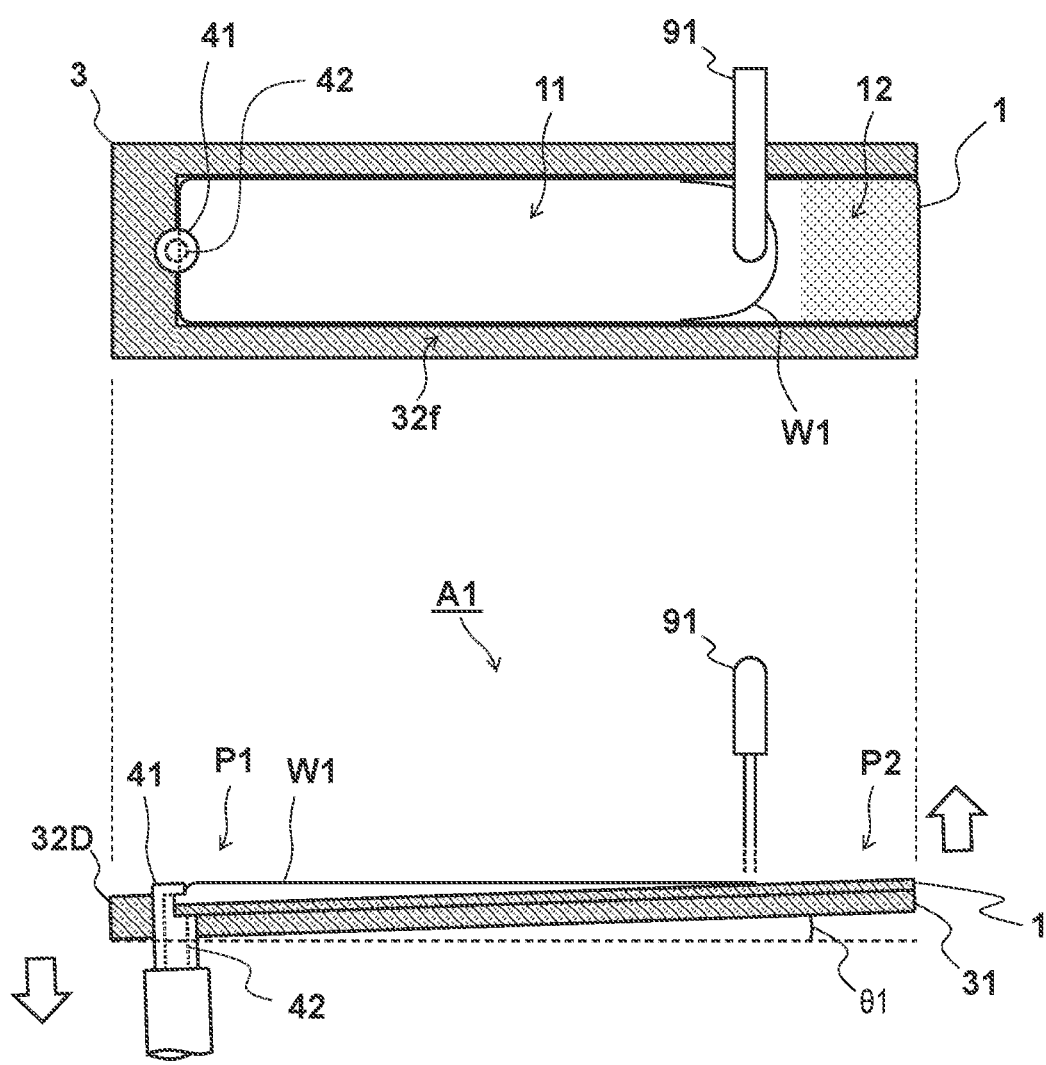
FIG. 2C shows a schematic top view and a schematic sectional view for explaining a step of the sample producing method.

FIG. 2C shows a top view and a sectional view showing a step of tilting the plate 1 arranged in the step shown in FIG. 2B together with the base plate 3 and then supplying a liquid onto the plate 1. First, the base plate 3 and the plate 1, which are in a horizontal posture, are tilted in directions indicated by arrows in FIG. 2C (first tilting step). Accordingly, the position of the end portion P1 of the plate 1 becomes lower than the position of the end portion P2. By the first tilting step, first, the plate 1 in the horizontal posture is set to a tilt posture A1 at a predetermined tilt angle (tilt angle $\theta1$). The tilt angle (the angle made by the surface (upper surface) of the plate 1 and the level surface: $\theta1$) of the plate 1 at this time is preferably, for example, about 0.5 to 5 [degrees] and is about 1 [degree] in this embodiment. Here, tilting of the plate 1 in the first tilting step can be performed by lowering only the side of the end portion P1, by raising only the side of the end portion P2, or by lowering the side of the end portion P1 and raising the side of the end portion P2.

Next, a liquid is supplied onto the plate 1 in the tilt posture A1 using a liquid supply unit 91. As described above, since the base plate 3 includes the frame portion 32 having a lyophobic property, as for the liquid supplied onto the plate 1, the supplied liquid is blocked by (the inner peripheral surface of the wall body of) the frame portion 32 and appropriately retained in a desired region of the plate 1, thereby forming a liquid pool W1 on the plate 1. More specifically, the supplied liquid is repelled by the lyophobic effect of the frame portion 32 and retained on the plate 1, and the liquid pool W1 is formed such that the surface (the surface on which the observation target object is placed) of the retained liquid is located at a position on the upper side of the surface of a surface portion 32f of the frame portion 32. Since the plate 1 is in the tilt posture A1, the depth (liquid depth) of the liquid of the liquid pool W1 is shallower on the side of the end portion P2 than on the side of the end portion P1. A solution or drug liquid having no substantial chemical effect on the observation target object (to be described later) can be used as the liquid. In this embodiment, pure water is used. As another embodiment, a physiological saline solution or the like may be used.

FIG. 2D shows a top view and a sectional view showing a step of placing the observation target object 2 on the liquid pool W1 formed in the step shown in FIG. 2C. The user places the observation target object 2 on the liquid pool W1 (and above the placement portion 11) using a predetermined tool 92. As the tool 92, a tool capable of handling the observation target object 2, for example, tweezer can be used. At this time, since the liquid depth of the liquid pool W1 is shallower on the side of the end portion P2 than on the side of the end portion P1, as described above, the observation target object 2 is arranged close to the surface of the plate 1 in the tilt posture A1 at least on the side of the end portion P2. Alternatively, the observation target object 2 may partially sink in the liquid pool W1 and may therefore directly contact the surface of the plate 1 in the tilt posture A1 in a part on the side of the end portion P2.

Figure 2E:
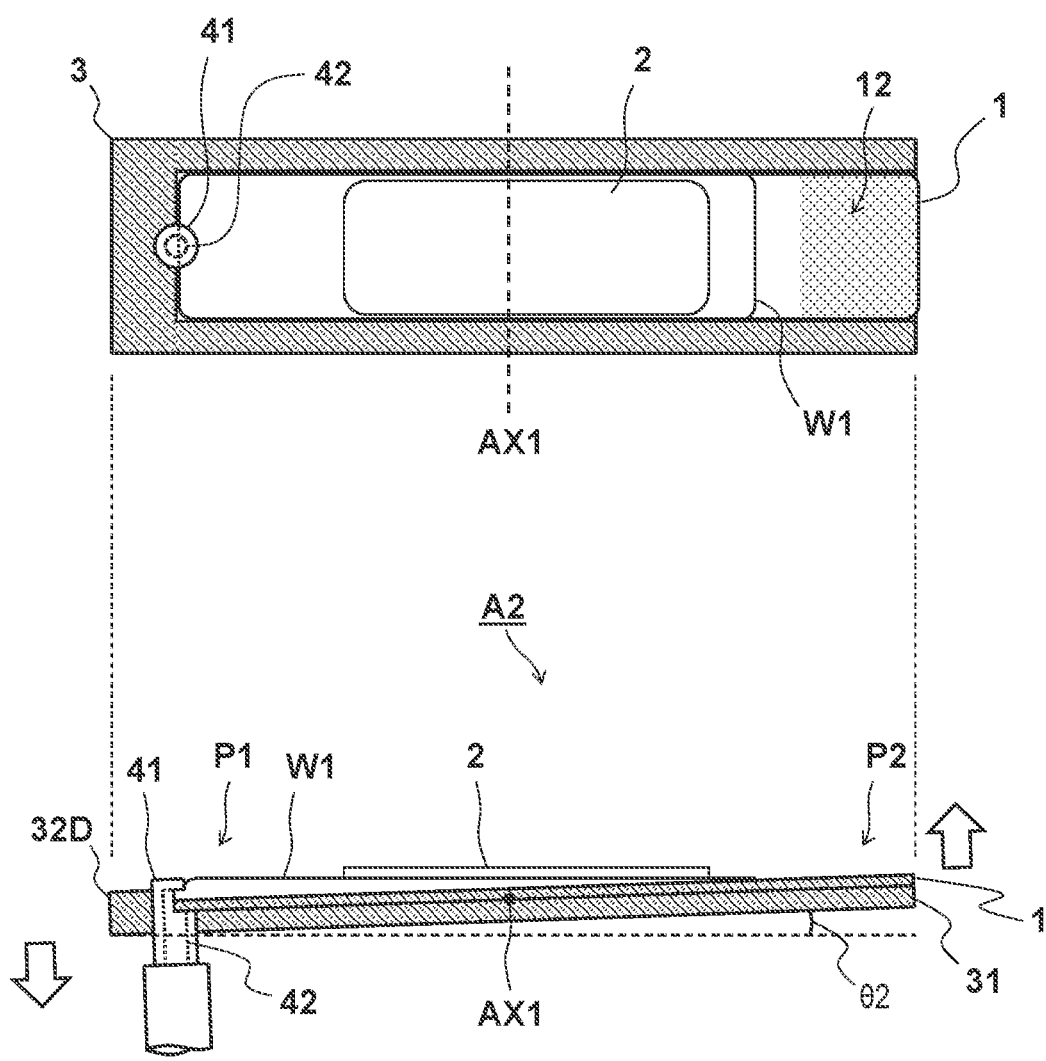
FIG. 2E shows a schematic top view and a schematic sectional view for explaining a step of the sample producing method.

FIG. 2E shows a top view and a sectional view showing a step of further tilting the plate 1 on which the observation target object 2 is placed on the liquid pool W1 in the step shown in FIG. 2D and starting discharge of the liquid of the liquid pool W1 on the plate 1. That is, the user makes the tilt angle of the plate 1 larger than in the tilt posture A1 at a desired timing, and the plate 1 is set in a tilt posture A2 at a tilt angle $\theta2$ ($>\theta1$). Accordingly, the liquid of the liquid pool W1 is guided to the liquid discharge mechanism 4 and the operation of the suction driving mechanism of the suction nozzle 41 is controlled, thereby starting suction (liquid discharge) of the liquid via the suction nozzle 41.

The operation of tilting the plate 1 from the tilt posture A1 to the tilt posture A2 and the operation of discharging the liquid via the suction nozzle 41 may be started almost simultaneously. However, the start timings need not always match, and the operations need only be executed at least at partially overlapping timings. Typically, the operation of tilting the plate 1 from the tilt posture A1 to the tilt posture A2 may be started after the elapse of a predetermined time from the start of the discharge operation of the liquid from the suction nozzle 41 so the liquid of the liquid pool W1 does not flow from above the frame portion 32 of the base plate 3.

Here, when tilting the plate 1 from the tilt posture A1 to the tilt posture A2, the plate 1 may be made to pivot using a line parallel to the surface of the plate 1 as an axis. In this embodiment, as shown in the sectional view of FIG. 2E, the plate 1 is made to pivot using a line parallel to the short side of the plate 1 having the rectangular shape as a pivot axis AX1 in a side view. The pivot axis AX1 of the plate 1 is set such that when tilting the plate 1 to discharge the liquid, the liquid retained on the surface of the plate 1 can continuously move toward the discharge port (the suction nozzle 41 in this embodiment). This allows the liquid to be continuously retained to the side of the suction nozzle 41. It is also possible to efficiently guide the liquid to the discharge port even if the amount of the discharged liquid deceases and efficiently perform the liquid discharge processing. More preferably, when the pivot axis AX1 of the plate 1 is set on the same plane as the surface of the plate 1 and also set in be parallel to a line perpendicular to a line passing through the center of the channel 42 (hole 311) in the side view, the liquid discharge processing can be performed more efficiently.

Figure 2F:
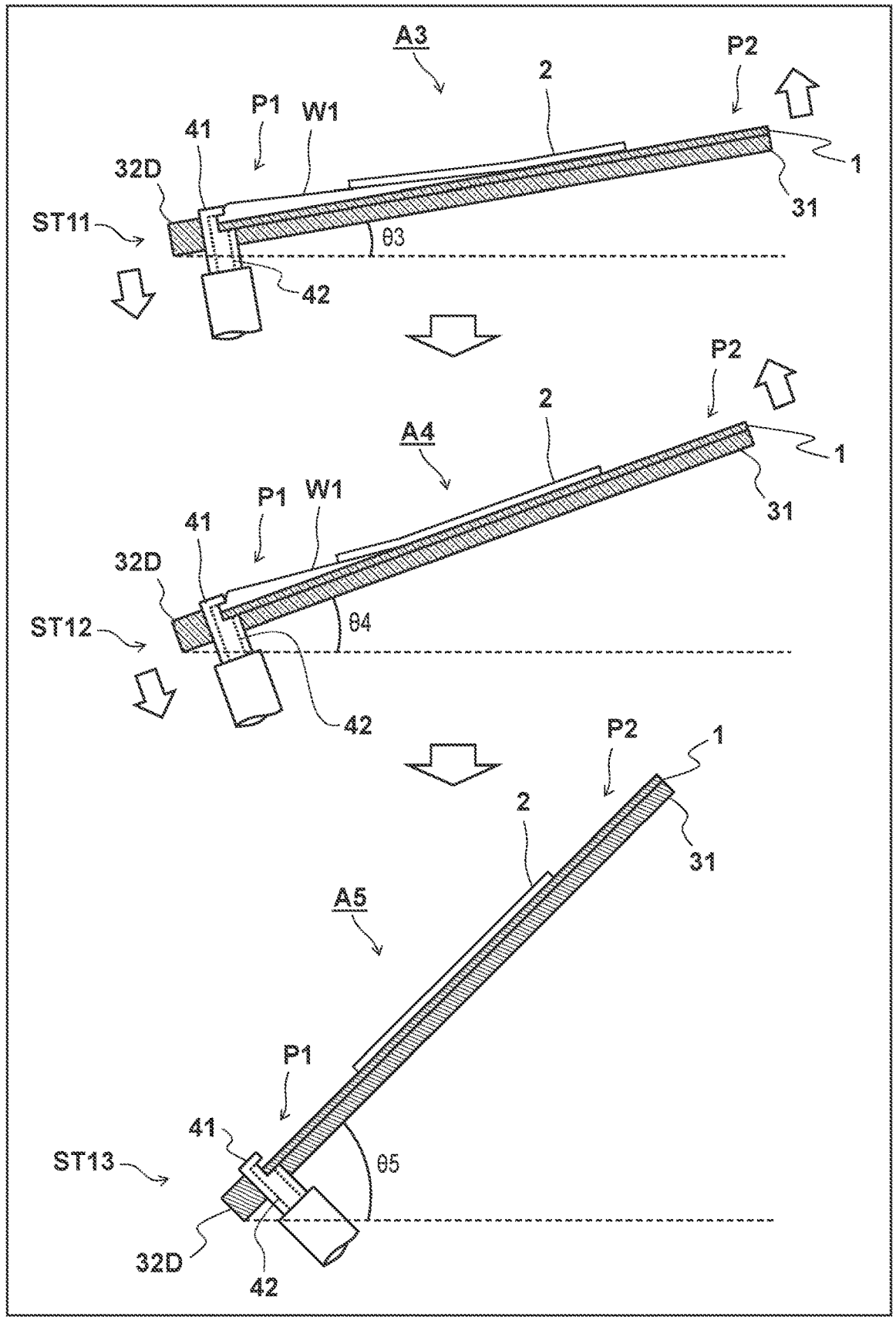
FIG. 2F is a schematic sectional view for explaining a step of the sample producing method.

FIG. 2F is a sectional view showing a step of further tilting the plate 1 from the step shown in FIG. 2E to promote the discharge of the liquid of the liquid pool W1 on the plate 1 until completion. The tilt angle of the plate 1 is made larger than in the tilt posture A2, and the plate 1 is set in a tilt posture A3 at a tilt angle $\theta3$ ($>\theta2$). In a state ST11 of the tilt posture A3, the liquid height level of the liquid lowers along with the increase of the tilt angle and/or the discharge of the liquid of the liquid pool W1 (the liquid moves from the side of the end portion P2 to the side of the end portion P1). Hence, the observation target object 2 on the liquid pool W1 directly contacts the surface of the plate 1 in the tilt posture A3 on the side of the end portion P2, and/or the contact area becomes large. On the other hand, on the side of the end portion P1, the observation target object 2 is still located on the liquid pool W1.

After that, the tilt angle of the plate 1 is made larger than in the tilt posture A3, and the plate 1 is set to a tilt posture A4 at a tilt angle θ4 (>θ3). In a state ST12 of the tilt posture A4, the area of contact between the observation target object 2 on the liquid pool W1 and the surface of the plate 1 in the tilt posture A4 becomes larger. Accordingly, the observation target object 2 can be attached to the surface of the plate 1 without causing wrinkles or twists in the observation target object 2.

After that, the tilt angle of the plate 1 is made larger than in the tilt posture A4, and the plate 1 is set to a tilt posture A5 at a tilt angle θ5 (>θ4). In a state ST13 of the tilt posture A5, the liquid pool W1 on the plate 1 is appropriately removed, that is, the discharge of the liquid of the liquid pool W1 is completed, and an observation sample SP is produced. The tilt angle θ5 of the plate 1 at the completion of the discharge of the liquid is, for example, about 40 to 60 [degrees] and is about 45 [degrees] in this embodiment.

As a summary, in the steps shown in FIGS. 2E and 2F, the observation target object 2 is continuously attached to the surface of the plate 1 from the end portion P2 toward the end portion P1. This makes it possible to finally fix the observation target object 2 to the surface of the plate 1. Hence, according to the above-described sample producing method, it is possible to discharge the unmercenary liquid from the surface of the plate 1 and also appropriately fix the observation target object 2 to the surface of the plate 1. Hence, the observation target object 2 whose wrinkles and twists are eliminated is placed and held on the placement surface of the plate 1, and the observation sample SP optimum for observation can be produced.

Also, the liquid discharge operation according to this embodiment is performed by changing the posture of the base plate 3 from the tilt posture A1 to the tilt posture A5 in the first tilting step. However, the sample producing method is not limited to this. For example, a similar liquid discharge operation can be performed by performing liquid discharge while maintaining the posture of the base plate 3 in the state of the tilt posture A1 and gradually increasing the suction force of the suction nozzle 41.

The above-described sample producing method includes placing the observation target object 2 on the surface of the liquid pool W1 on the plate 1 (the step shown in FIG. 2D), and making the amount of the liquid of the liquid pool W1 larger on the side of the end portion P1 than on the side of the end portion P2 and attaching and fixing the observation target object 2 to the surface of the plate 1 sequentially from the end portion P2 toward the end portion P1 (the steps shown in FIGS. 2E and 2F). According to this sample producing method, after the observation target object 2 is partially brought into contact with the surface of the plate 1 on the liquid discharge upstream side, the observation target object 2 comes into contact with the plate surface sequentially from the liquid discharge upstream side toward the liquid discharge downstream side. As a result, it is possible to fix the observation target object 2 onto the plate 1 without causing wrinkles or twists in the observation target object 2. That is, it is possible to reliably and easily produce the observation sample SP.

In this embodiment, in the steps shown in FIGS. 2E and 2F, the plate 1 is tilted to discharge the liquid of the liquid pool W1 from the side of the end portion P1, thereby appropriately eliminating wrinkles, twists, and the like in the observation target object 2. The discharge of the liquid is promoted such that the liquid depth of the liquid pool W1 on the plate 1 becomes shallower on the side of the end portion P2 than on the side of the end portion P1, thereby lowering the liquid height level of the liquid pool W1. From this viewpoint, it can be said that further tilting the plate 1 in the step shown in FIG. 2E is equivalent to requesting to start varying the amount of the liquid of the liquid pool W1 (start discharging the liquid). According to this procedure, the observation target object 2 continuously comes into contact with the plate surface from the liquid discharge upstream side toward the liquid discharge downstream side.

In this embodiment, the plate 1 has a rectangular shape with long sides and short sides, and when tilting the plate 1, the plate 1 is made to pivot while setting a line parallel to the short side of the plate 1 to a pivot axis. However, a line parallel to the long side may be set to the pivot axis. That is, in this embodiment, the liquid discharge direction is parallel to the long side direction of the plate 1. As another embodiment, the liquid discharge direction may be parallel to the short side direction of the plate 1. In other words, the pivot axis may be set such that the liquid discharge direction is set to the opposite side direction. Alternatively, the position of the hole 311 may be offset to the side of the edge portion 32S1 (or 32S2), and the pivot axis may be set such that the liquid discharge direction is set to the diagonal direction.

Also, in this embodiment, the suction nozzle 41 is used to discharge the liquid. Alternatively, the liquid may be discharged by an opening/closing operation of a known valve that can be installed in the channel 42. This may simplify the liquid discharge mechanism 4.

Modification of First Embodiment

Figure 3A:
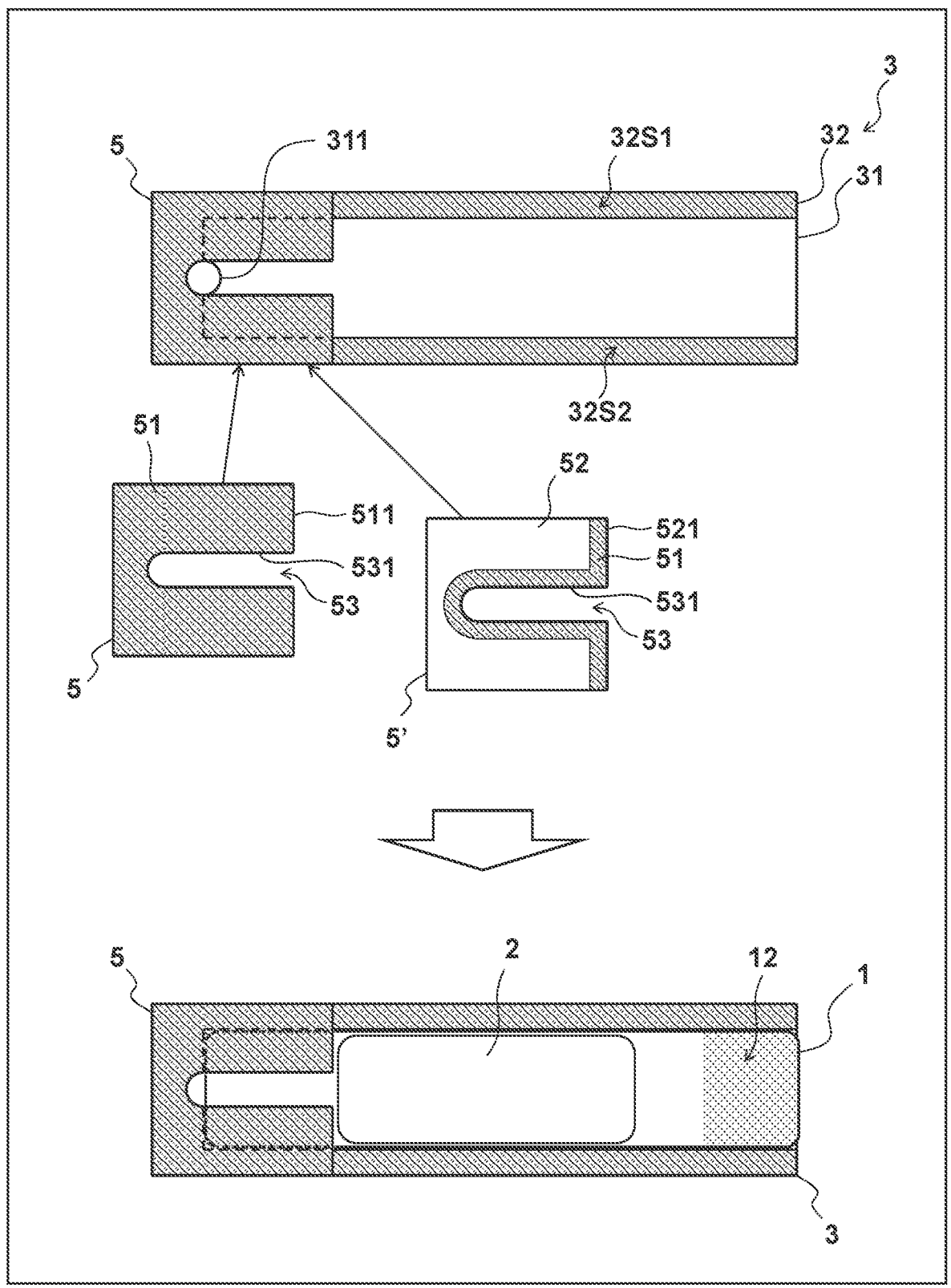
FIG. 3A is schematic top view for explaining an example of a lyophobic plate member applicable to the base plate and an example of an observation target object in a case in which the lyophobic plate member is applied.

When performing the sample producing method according to the embodiment, an external member may additionally be applied to the base plate 3. FIG. 3A shows top views showing, as an example, a configuration in which a lyophobic plate member 5 is applied to the base plate 3. The lyophobic plate member 5 is a plate member having a predetermined thickness. The lower surface (the surface on the side of the base plate 3) is formed into a shape engaging with the support portion 31 and the frame portion 32. That is, a portion facing the frame portion 32 is recessed and thin relative to the portion facing the support portion 31. At least a part of the lyophobic plate member 5 is made of a lyophobic material, like the frame portion 32. In this embodiment, the lyophobic plate member 5 is a plate member having an almost square shape in the top view, and at least the upper surface and the lower surface, and the whole surface of a distal end side surface 511 (the right end side surface in FIG. 3A) are formed as a lyophobic portion 51 having a lyophobic property. The lyophobic plate member 5 has a cut portion 53 extending from the distal end side surface 511 toward the base end side surface (the left end side surface in FIG. 3A). The cut portion 53 is formed into a cut having a predetermined length to expose, at its distal end, the hole 311 in which the liquid discharge mechanism 4 is installed. A wall surface 531 of the cut portion 53 is also included in the lyophobic portion 51.

With the above-described configuration, the lyophobic plate member 5 regulates the movement of the observation target object 2 during production of the observation sample SP. Hence, the observation target object 2 continuously stays at the center of the plate 1 in the longitudinal direction during the discharge process of the liquid of the liquid pool W1. As a result, the observation target object 2 is fixed to the center of the plate 1. Note that the lyophobic plate member 5 may wholly be made of the lyophobic material, as a matter of course.

As indicated by an arrow, FIG. 3A also shows, as a subsequent state, a state in which the plate 1 is placed on the base plate 3 on which the lyophobic plate member 5 is arranged, and the observation target object 2 is placed at a predetermined position on the plate 1. When the base plate 3 is used, in the steps shown in FIGS. 2E and 2F, it is possible to appropriately regulate the movement of the observation target object 2 caused by the discharge of the liquid of the liquid pool W1.

The lyophobic plate member 5 need only be configured to be able to regulate the movement of the observation target object 2 during production of the observation sample SP. Hence, a lyophobic plate member 5' may be used in place of the lyophobic plate member 5. The lyophobic plate member 5' includes the lyophobic portion 51 that causes a part of the edge portion on the upper surface to have the lyophobic property, and a main body portion 52 other than the lyophobic portion 51. More specifically, the main body portion 52 has the cut portion 53 extending from the distal end side surface (the right end side surface in FIG. 3A) toward the base end side surface (the left end side surface in FIG. 3A). The cut portion 53 is formed into a cut having a predetermined length to expose, at its distal end, the hole 311 in which the liquid discharge mechanism 4 is installed. In the lyophobic plate member 5', the distal end side surface, the upper and lower surfaces on the periphery of the distal end side surface, the wall surface 531 of the cut portion 53, and the upper and lower surfaces on the periphery of the wall surface 531 are formed as the lyophobic portion 51. As the constituent material of the main body portion 52, a material whose lyophobic property is lower than the lyophobic portion 51 can be used, and a material without the lyophobic property, a material having a hydrophilic property, or the like may be used.

Figure 3B:
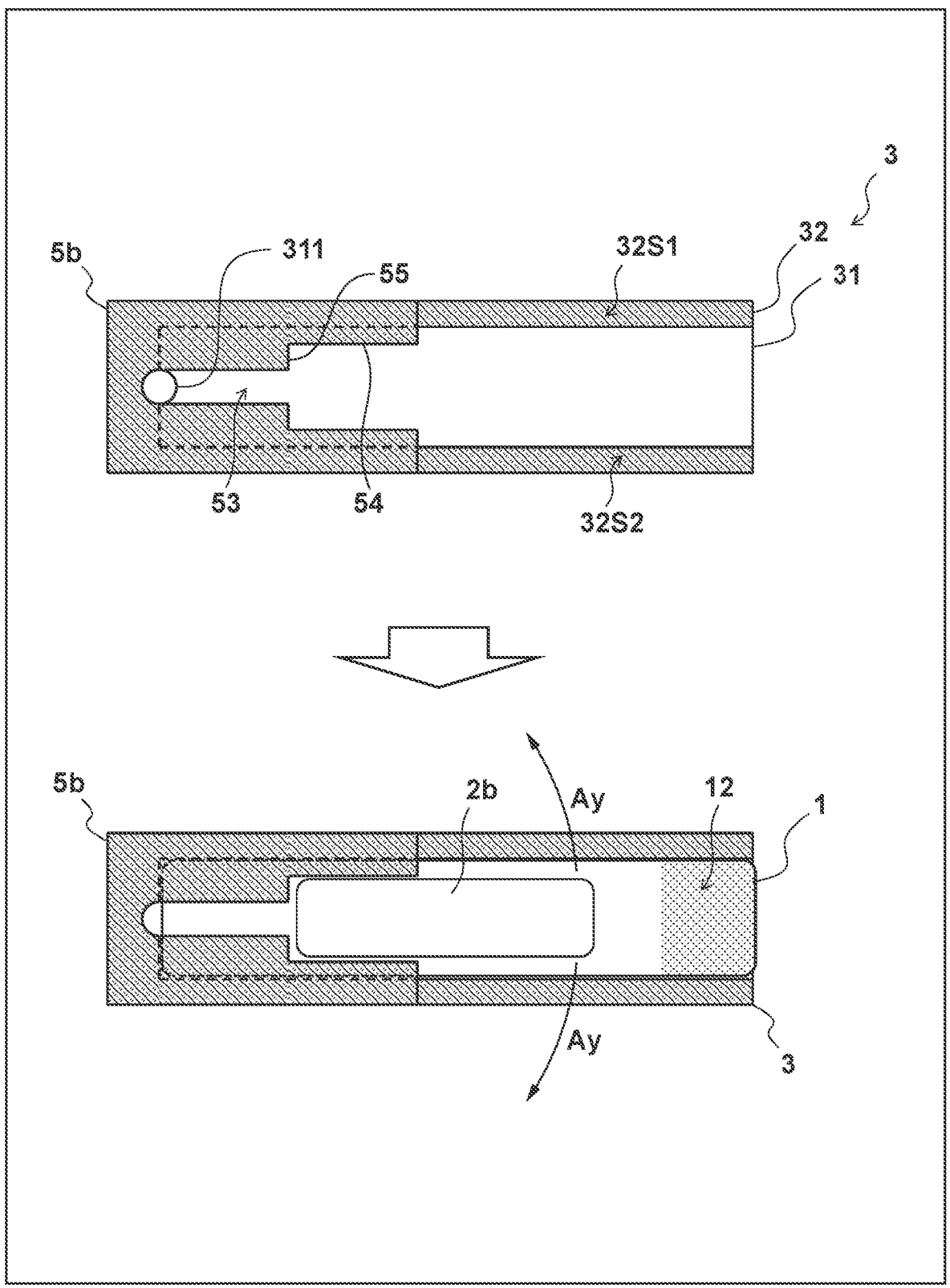
FIG. 3B is a schematic top view for explaining an example of a lyophobic plate member applicable to the base plate and an example of an observation target object in a case in which the lyophobic plate member is applied.

FIG. 3B shows a configuration in a case in which a lyophobic plate member 5b according to another example is arranged on the base plate 3. The lyophobic plate member 5b is provided longer in the longitudinal direction than the lyophobic plate member 5, and includes a widened cut portion 54 that regulates the movement of an observation target object (observation target object 2b) in the widthwise direction. The widened cut portion 54 is formed wide from a halfway of the cut portion 53. According to this shape, the observation target object 2b comes into contact with a step portion 55 between the cut portion 53 and the widened cut portion 54, and a part of the observation target object 2b is stored in the widened cut portion 54. Since a part of the observation target object 2b is guided by the widened cut portion 54, a rotation of the observation target object 2b in the direction of an arrow Ay is regulated. The longer the cut length of the widened cut portion 54 is, the higher the rotation suppressing effect is. As indicated by an arrow, FIG. 3B also shows, as a subsequent state, a state in which the plate 1 is placed on the base plate 3 on which the lyophobic plate member 5b is arranged, and the observation target object 2b whose width is relatively narrow is placed on the plate 1. That is, according to the example shown in FIG. 3B, it is possible to regulate the movement of the observation target object 2b in the widthwise direction, which cannot be dealt by the edge portions 32S1 and 32S2 of the frame portion 32.

Figure 3C:
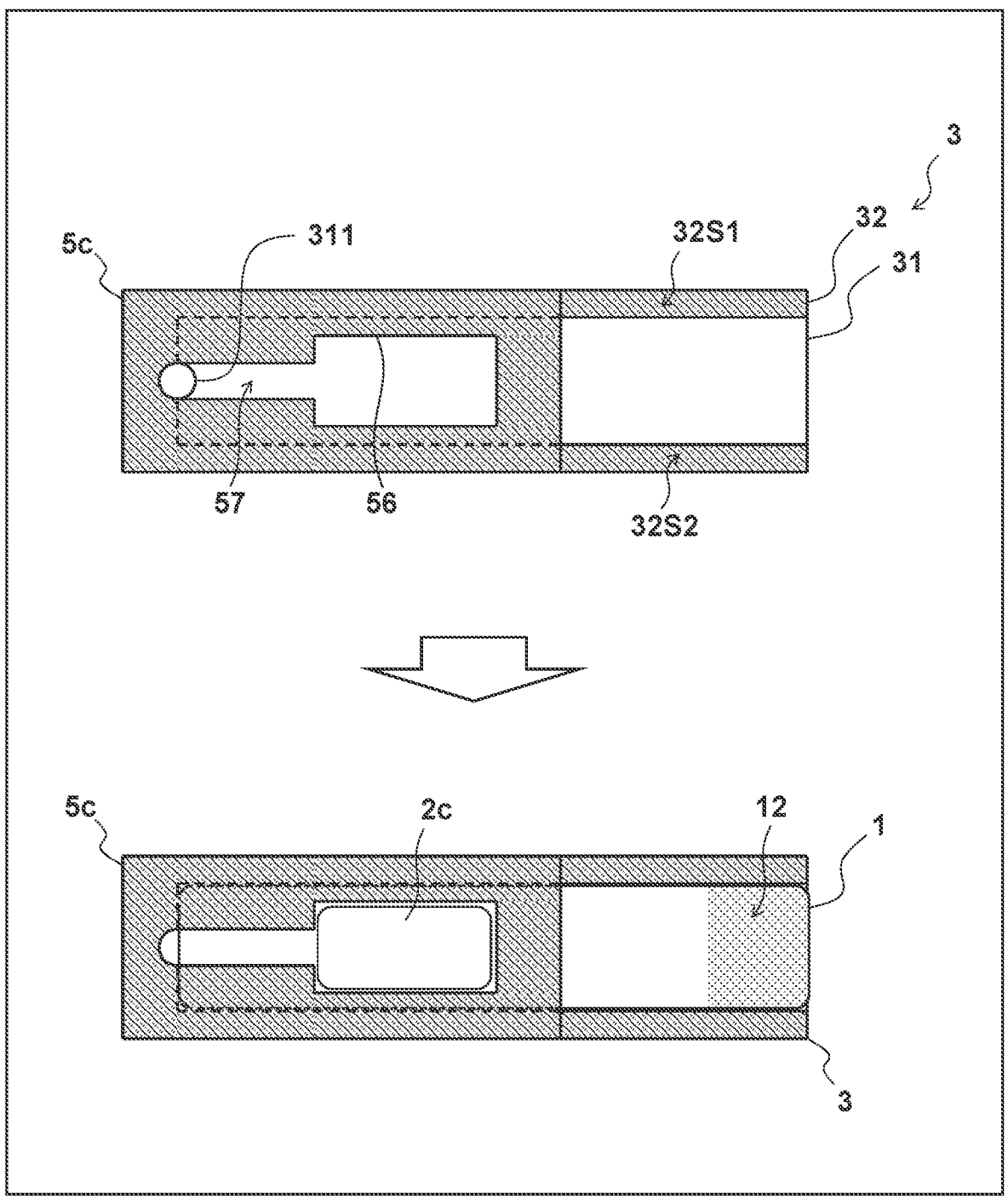
FIG. 3C is a schematic top view for explaining an example of a lyophobic plate member applicable to the base plate and an example of an observation target object in a case in which the lyophobic plate member is applied.

FIG. 3C shows a configuration in a case in which a lyophobic plate member 5c according to still another example is arranged on the base plate 3. The lyophobic plate member 5c includes a restriction portion 56 that completely regulates the movement of an observation target object (observation target object 2c) in the longitudinal direction and the widthwise direction. The restriction portion 56 is an opening formed almost at the center of the lyophobic plate member 5c, and is formed into almost the same shape and size as the observation target object 2c. The lyophobic plate member 5c also has a cut portion 57 extending from the base end side surface (the left end side surface in FIG. 3C) of the restriction portion 56 toward the hole 311. The cut portion 57 is formed into a cut having a predetermined length to expose, at its distal end, the hole 311 in which the liquid discharge mechanism 4 is installed. As indicated by an arrow, FIG. 3C also shows, as a subsequent state, a state in which the plate 1 is placed on the base plate 3 on which the lyophobic plate member 5c is arranged, and the observation target object 2c whose size is smaller than the observation target object 2 and the observation target object 2b is placed on the plate 1. That is, according to the example shown in FIG. 3C, the movement of the observation target object 2c in any direction can be regulated. Note that in the example shown in FIG. 3C, since the observation target object 2c is surrounded, on whole periphery, by the lyophobic plate member 5c, the frame portion 32 of the base plate 3 need not be lyophobic.

As described above, the external member applicable to the base plate 3 is not limited to the lyophobic plate member 5 (or 5'), and one of a plurality of members having various shapes can selectively be applied to the base plate 3 in accordance with the size of the observation target object 2. It is therefore possible to retain the liquid in a desired region on the plate 1, and simultaneously prevent the movement of the observation target object 2 or the like from a predetermined position at the time of discharge of the liquid and optimally place the observation target object at a desired position on the surface of the plate 1.

From the viewpoint of regulating the movement of the observation target object 2, a part/whole part of the above-described frame portion 32 may be provided integrally with the lyophobic plate member 5 or the like. That is, in the step shown in FIG. 2A (the step of preparing the base plate 3), the frame portion 32 according to the size of the observation target object 2 may be arranged together with the lyophobic plate member 5 or the like on the support portion 31 to form the base plate 3.

Second Embodiment

Figure 4A:
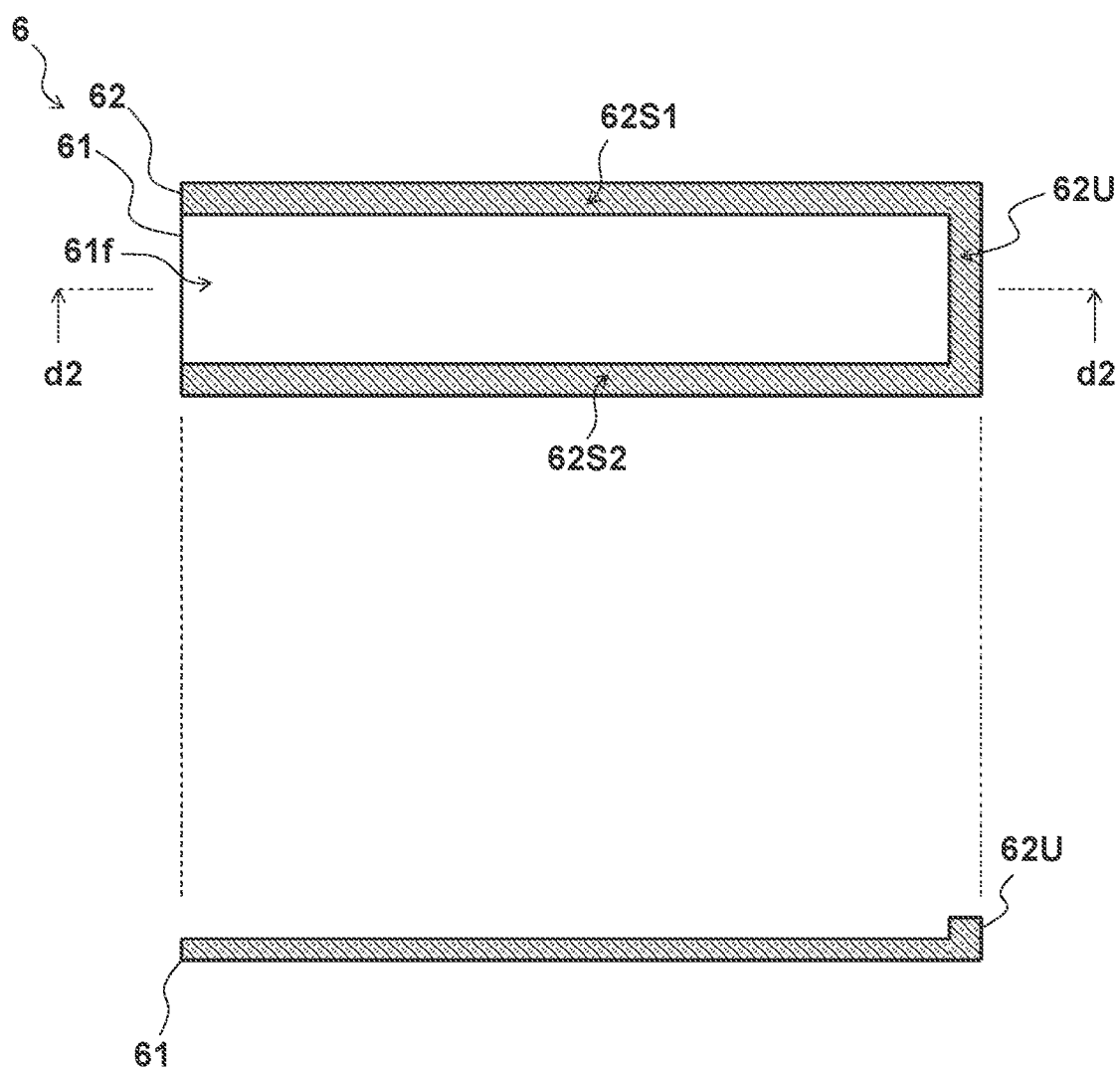
FIG. 4A shows a schematic top view and a schematic sectional view for explaining a step of a sample producing method.

The sample producing method according to the above-described first embodiment can also be implemented using a base plate having a configuration different from the base plate 3. FIG. 4A shows a top view showing a step of preparing a base plate 6 used in a sample producing method according to the second embodiment and a sectional view taken along a line d2-d2 in the top view (to be simply referred to as a "sectional view" hereinafter, and this also applies to the remaining sectional views in this embodiment).

The base plate 6 includes a support portion 61 and a frame portion 62. As the relationship with the first embodiment (see FIG. 1A and the like), the support portion 61 is the same as the support portion 31 except that the hole 311 is not provided. The frame portion 62 is a U-shaped wall body provided from the upper surface of the support portion 61 to surround three sides of the base plate 6 (such that the open side is formed on the liquid discharge downstream side in this embodiment). The support portion 61 and the frame portion 62 are integrally provided. The frame portion 62 includes an edge portions 62U, 62S1, and 62S2. As the relationship with the first embodiment (see FIG. 1A and the like), the edge portion 62U is provided on the opposite side of the edge portion 32D. On the other hand, the edge portions 62S1 and 62S2 are the same as the edge portions 32S1 and 32S2, respectively.

That is, no wall body exists on one end portion side (the left side in FIG. 4A) in the longitudinal direction of the support portion 61, and the frame portion 62 is open in this portion. In this embodiment, in the base plate 6, a portion surrounded by the U-shaped frame portion 62 is a placement surface 61*f*. In other words, on the support portion 61, the edge portions 62U, 62S1, and 62S2 contact each other to form the U-shaped frame portion 62, and a portion other than the frame portion 62 is the placement surface 61*f* For a description to be omitted here, the contents of the first embodiment are invokable.

Figure 4B:
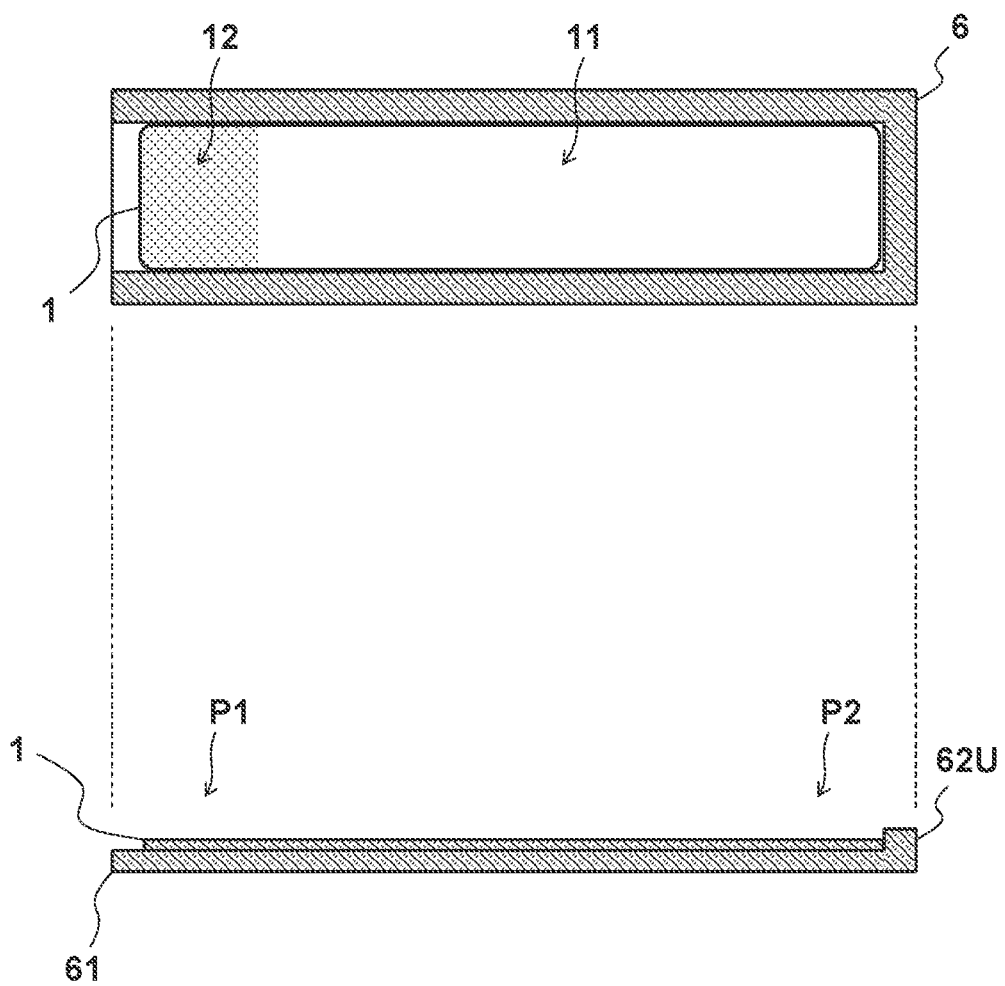
FIG. 4B shows a schematic top view and a schematic sectional view for explaining a step of the sample producing method.

FIG. 4B shows a top view and a sectional view showing a step of arranging a plate 1 on the base plate 6 prepared in the step shown in FIG. 4A. The plate 1 is arranged here such that a frosted portion 12 is located on the liquid discharge downstream side. However, the frosted portion 12 may be located on the liquid discharge upstream side. As in the first embodiment, one end portion P1 of the plate 1 corresponds to the liquid discharge downstream-side end portion, and the other end portion P2 on the opposite side (the opposite side of the end portion P1 with respect to the placement surface 61*f*) corresponds to the liquid discharge upstream-side end portion.

Figure 4C:
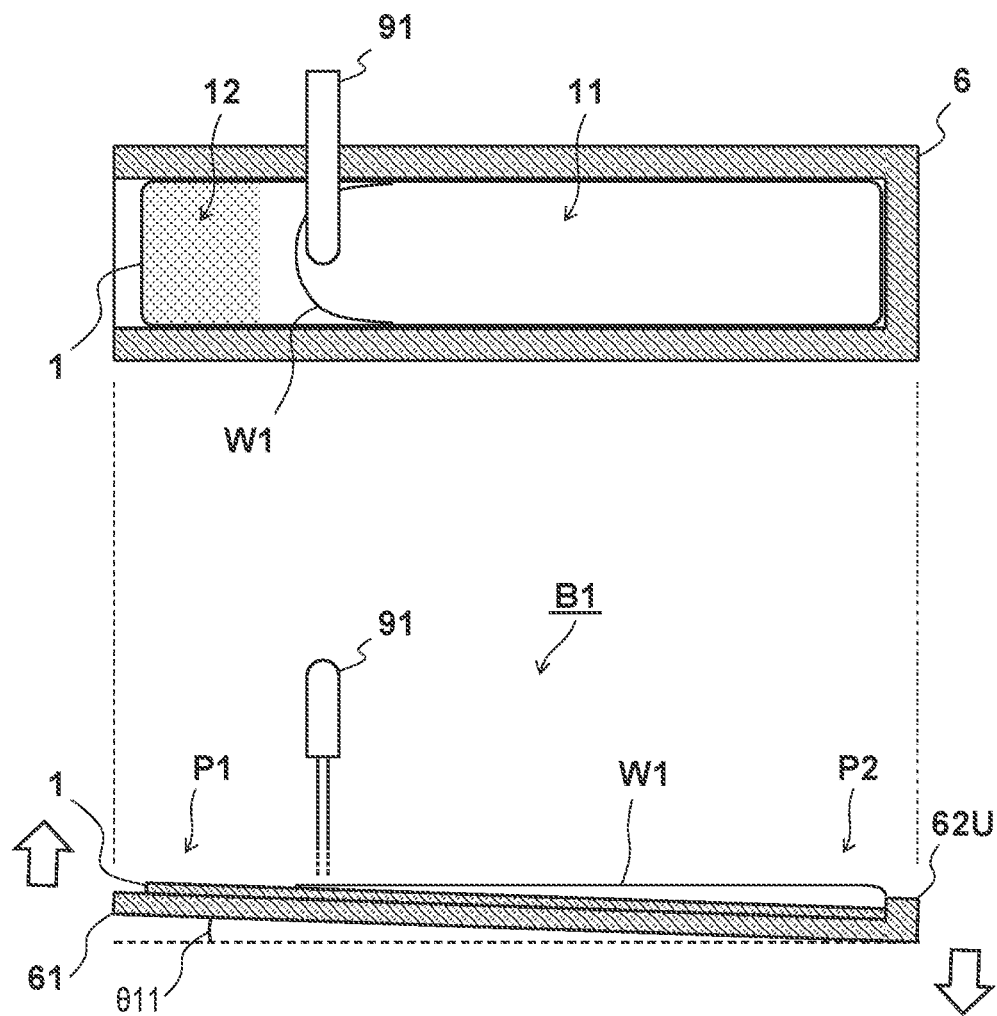
FIG. 4C shows a schematic top view and a schematic sectional view for explaining a step of the sample producing method.

FIG. 4C shows a top view and a sectional view showing a step of tilting the plate 1 arranged in the step shown in FIG. 4B together with the base plate 6 and then supplying a liquid onto the plate 1. First, the base plate 6 and the plate 1, which are in a horizontal posture, are tilted in directions indicated by arrows in FIG. 4C (second tilting step). Accordingly, the position of the end portion P1 of the plate 1 becomes higher than the position of the end portion P2. By the second tilting step, first, the plate 1 in the horizontal posture is set to a tilt posture B1 at a predetermined tilt angle (tilt angle θ11). The tilt angle θ11 of the plate 1 at this time is preferably, for example, about 0.5 to 5 [degrees] and is about 1 [degree] in this embodiment. Here, tilting of the plate 1 in the first tilting step can be performed by raising only the side of the end portion P1, by lowering only the side of the end portion P2, or by raising the side of the end portion P1 and lowering the side of the end portion P2.

Next, a liquid is supplied onto the plate 1 in the tilt posture B1 using a liquid supply unit 91. This forms a liquid pool W1 on the plate 1. Here, on the plate 1 in the tilt posture B1, the liquid depth of the liquid pool W1 is deeper on the side of the end portion P2 than on the side of the end portion P1.

Figure 4D:
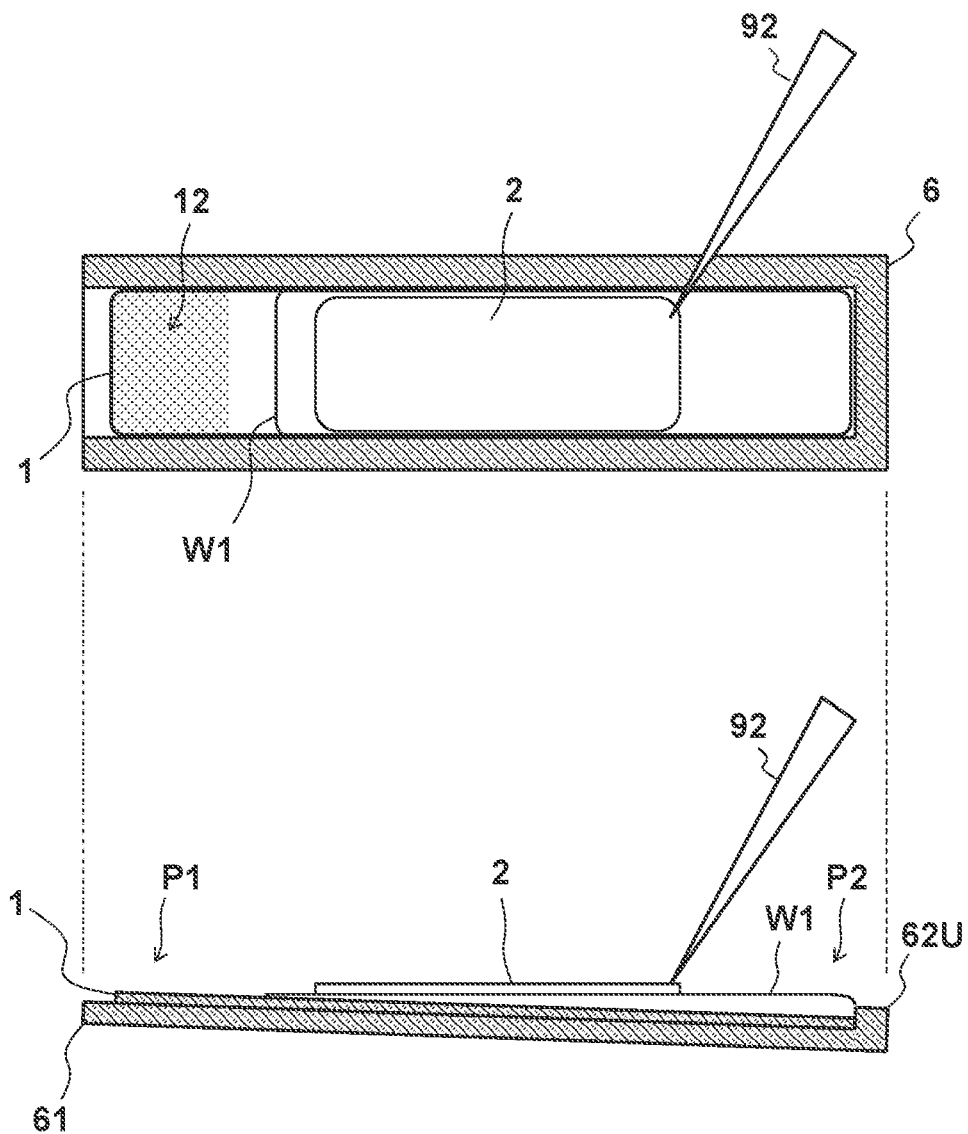
FIG. 4D shows a schematic top view and a schematic sectional view for explaining a step of the sample producing method.

FIG. 4D shows a top view and a sectional view showing a step of placing an observation target object 2 on the liquid pool W1 formed in the step shown in FIG. 4C. The user places the observation target object 2 on the liquid pool W1 (and above a placement portion 11) using a tool 92. Since the liquid depth of the liquid pool W1 is deeper on the side of the end portion P2 than on the side of the end portion P1, as described above, it can be said that the observation target object 2 is apart from the surface of the plate 1 in the tilt posture B1 on the side of the end portion P2.

Figure 4E:
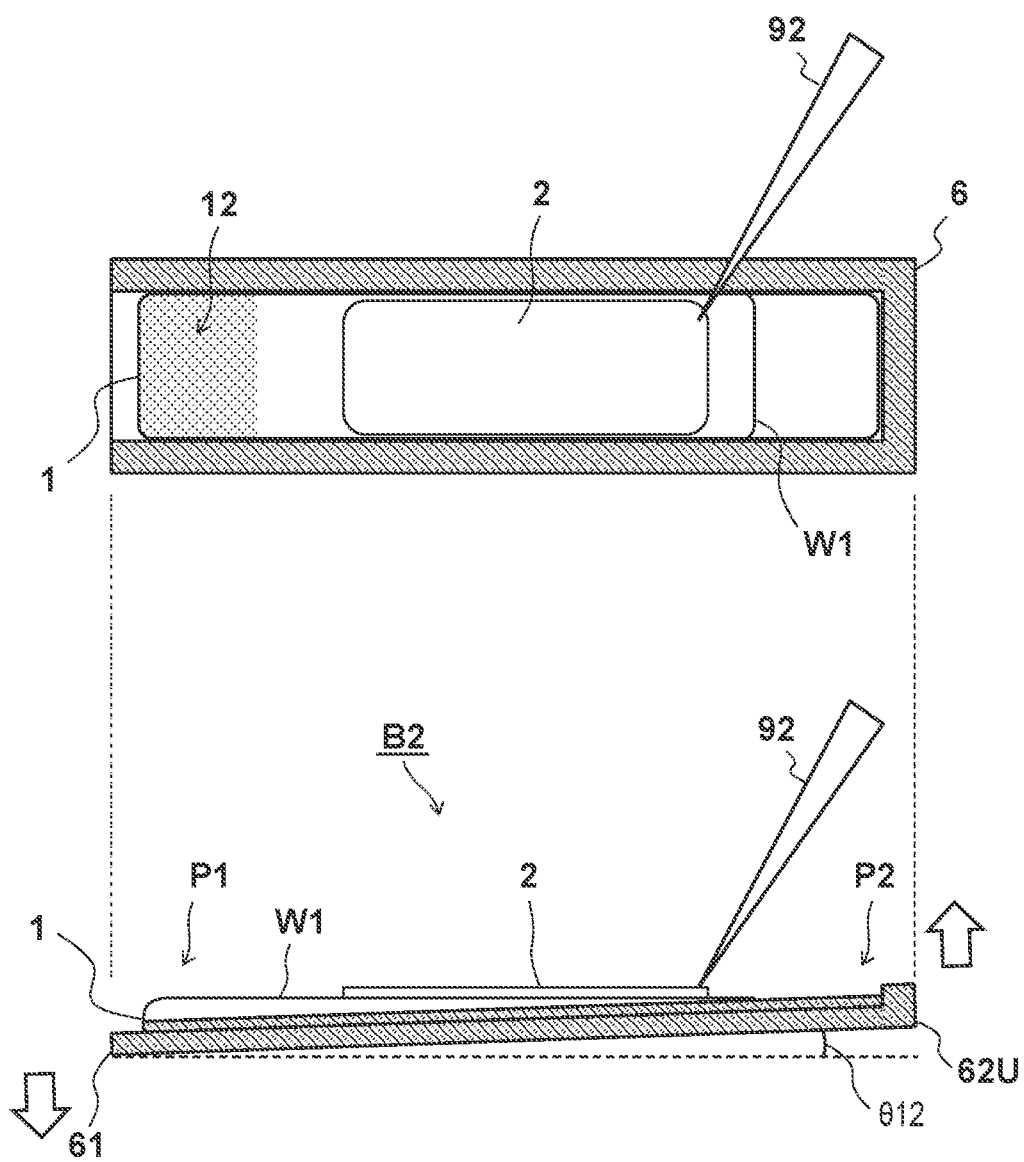
FIG. 4E shows a schematic top view and a schematic sectional view for explaining a step of the sample producing method.

FIG. 4E shows a top view and a sectional view showing a step of tilting the plate 1 on which the observation target object 2 is placed on the liquid pool W1 in the step shown in FIG. 4D and starting discharge of the liquid of the liquid pool W1 on the plate 1. First, the base plate 6 and the plate 1 in the tilt posture B1 are tilted in directions indicated by arrows in FIG. 4E (third tilting step). The directions of tilting the plate 1 in the third tilting step are directions opposite to the directions of tilting the plate 1 in the second tilting step. Accordingly, the position of the end portion P1 of the plate 1 becomes lower than the position of the end portion P2. By the third tilting step, the plate 1 in the tilt posture B1 is set to a tilt posture B2 at a predetermined tilt angle (tilt angle θ12).

In this step, the operator may press (or fix) the observation target object 2 to the side of the plate 1 using the tool 92 until the liquid depth of the liquid pool W1 at the end portion P2 becomes almost zero. Preferably, the observation target object 2 is preferably pressed to the side of the plate 1 until the observation target object 2 directly contacts the surface of the plate 1 in a part on the side of the end portion P2.

Figure 4F:
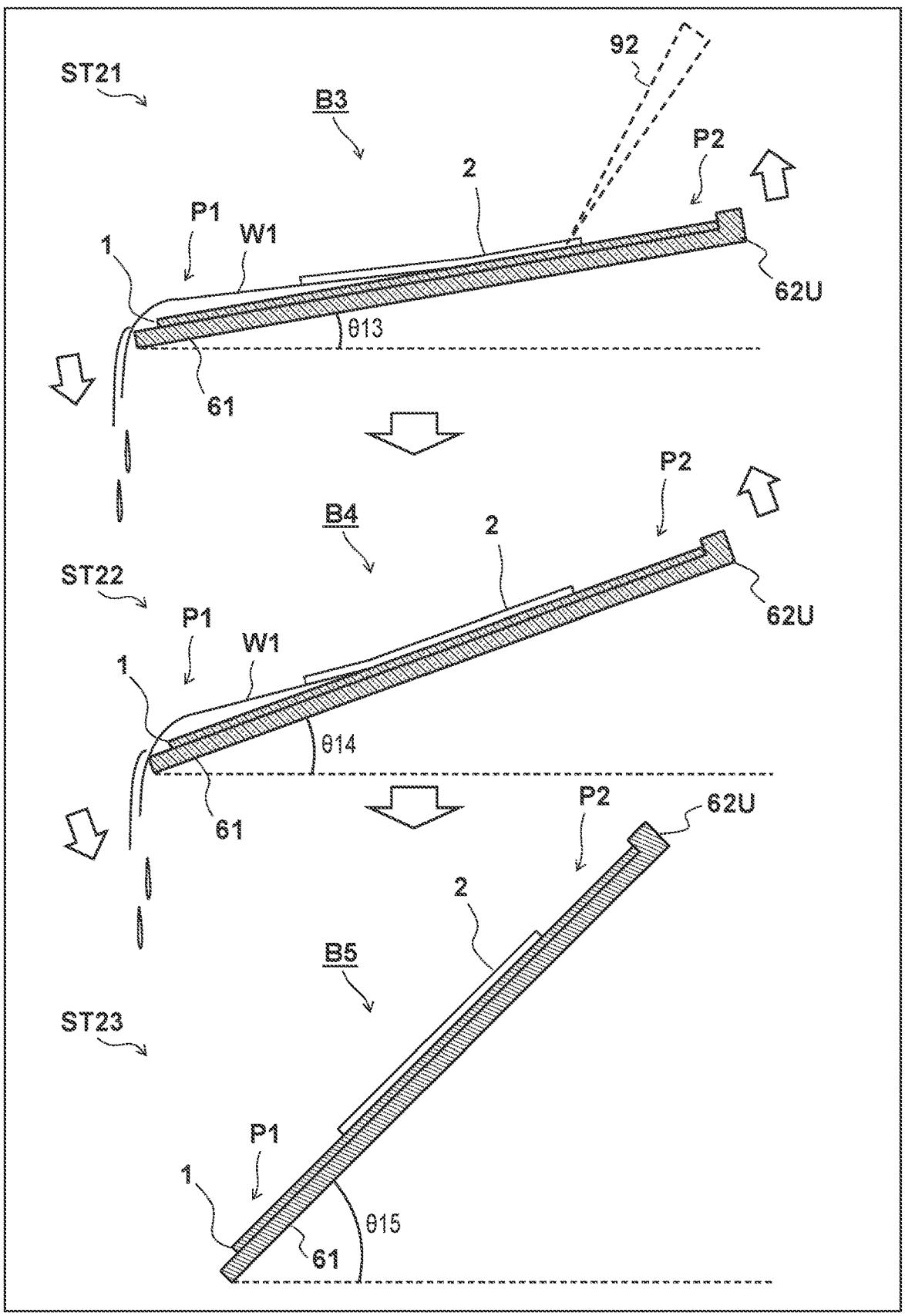
FIG. 4F is a schematic sectional view for explaining a step of the sample producing method.

FIG. 4F is a sectional view showing a step of further tilting the plate 1 from the step shown in FIG. 4E to promote the discharge of the liquid of the liquid pool W1 on the plate 1 until completion. The tilt angle of the plate 1 is made larger than in the tilt posture B2, and the plate 1 is set in a tilt posture B3 at a tilt angle θ13 (>θ12). In a state ST21 of the tilt posture B3, the liquid height level of the liquid lowers along with the increase of the tilt angle and/or the discharge of the liquid of the liquid pool W1 (the liquid moves from the side of the end portion P2 to the side of the end portion P1). Hence, the observation target object 2 on the liquid pool W1 directly contacts the surface of the plate 1 in the tilt posture B3 on the side of the end portion P2, and/or the contact area becomes large. On the other hand, on the side of the end portion P1, the observation target object 2 is still located on the liquid pool W1. Note that in this step, since the observation target object 2 is partially fixed to the plate surface at least on the liquid discharge upstream side, the user may separate the tool 92 from the observation target object 2.

After that, the tilt angle of the plate 1 is made larger than in the tilt posture B3, and the plate 1 is set to a tilt posture B4 at a tilt angle θ14 (>θ13). In a state ST22 of the tilt posture B4, the area of contact between the observation target object 2 on the liquid pool W1 and the surface of the plate 1 in the tilt posture B4 becomes larger. Accordingly, the observation target object 2 can be attached to the surface of the plate 1 without causing wrinkles or twists in the observation target object 2.

After that, the tilt angle of the plate 1 is made larger than in the tilt posture B4, and the plate 1 is set to a tilt posture B5 at a tilt angle θ15 (>θ14). In a state ST23 of the tilt posture B5, the liquid pool W1 on the plate 1 is appropriately removed, that is, the discharge of the liquid of the liquid pool W1 is completed, and an observation sample SP is produced. The tilt angle of the plate 1 at the completion of the discharge of the liquid is, for example, about 40 to 60 [degrees] and is about 55 [degrees] in this embodiment.

As a summary, in the steps shown in FIGS. 4E and 4F, the observation target object 2 is continuously attached to the surface of the plate 1 from the end portion P2 toward the end portion P1. This makes it possible to finally fix the observation target object 2 to the surface of the plate 1 evenly and tightly without causing wrinkles or twists. Hence, according to the above-described sample producing method as well, the observation target object 2 whose wrinkles and twists are eliminated is placed and held on the placement surface of the plate 1, the observation sample SP optimum for observation can be produced, and the same effects as in the above-described first embodiment can be obtained. Note that in this embodiment, to prevent the plate 1 from falling from the base plate 6 in the tilt posture in the steps shown in FIGS. 4E and 4F, a surface treatment may be performed for the surface of the frame portion 62, or the plate 1 may be held by a plate holding means (not shown).

Also, in this embodiment, after tilting is performed in the second tilting step such that the end portion P1 is located on the upper side, and the end portion P2 is located on the lower side, tilting is performed in the third tilting step such that the end portion P1 is located on the lower side, and the end portion P2 is located on the upper side. Accordingly, the liquid is moved to the side of the end portion P2 and then moved to the side of the end portion P1. As a result, the observation target object 2 can be reliably and easily fixed to the plate 1.

As described above, according to the sample producing method of this embodiment, it is possible to obtain the same effects as in the first embodiment, and it is also possible to reliably and easily fix the observation target object 2 to the plate 1 by moving the liquid first to the side of the end portion P2 and then to the side of the end portion P1.

Application Examples

Various changes can be made for the above-described embodiments. For example, the sample producing method according to each embodiment may partially be changed by changing the structure of the base plate 3 or 6.

Figure 5A:
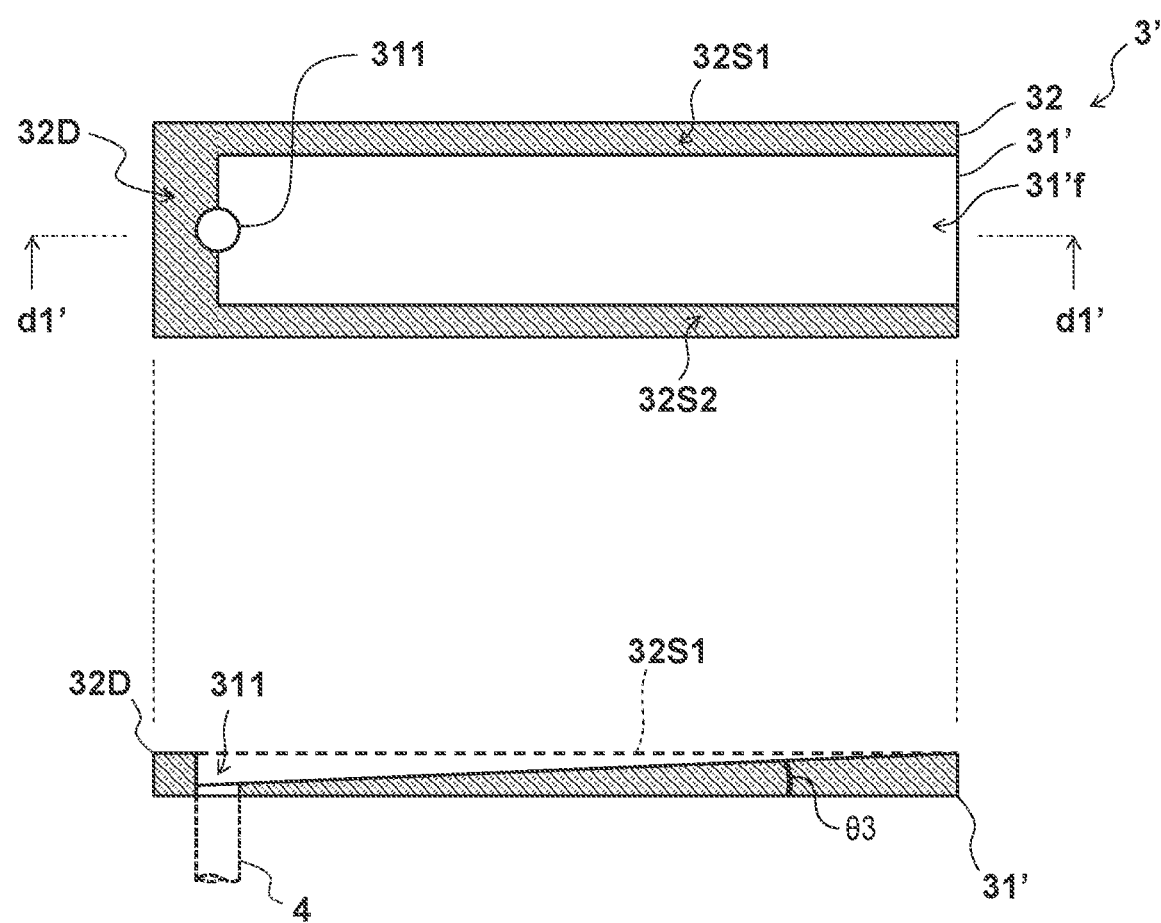
FIG. 5A shows a schematic top view and a schematic sectional view of the configuration of a base plate.

FIG. 5A shows a top view of a base plate 3' as another example of the base plate usable in the sample producing method according to the first embodiment and a sectional view taken along a line d1'-d1' in the top view. The base plate 3' is different from the base plate 3 (see FIG. 1A and the like) according to the first embodiment in that, in place of the support portion 31, the base plate 3' includes a support portion 31' whose upper surface is a tilting surface provided at a predetermined tilt angle (tilt angle θ3) in advance in the horizontal posture. That is, the base plate 3' is provided such that the support portion 31' gradually becomes thicker (the thickness of the support portion 31' increases) from one end portion on the side of the hole 311 in which the liquid discharge mechanism 4 can be installed to the other end portion on the opposite side (the opposite side of the one end portion with respect to a placement surface 31'f). The tilt angle θ3 of the upper surface of the support portion 31' can be about 1 degree. Note that the frame portion 32 is the same as in the base plate 3 (see FIG. 1A and the like).

Figure 5B:
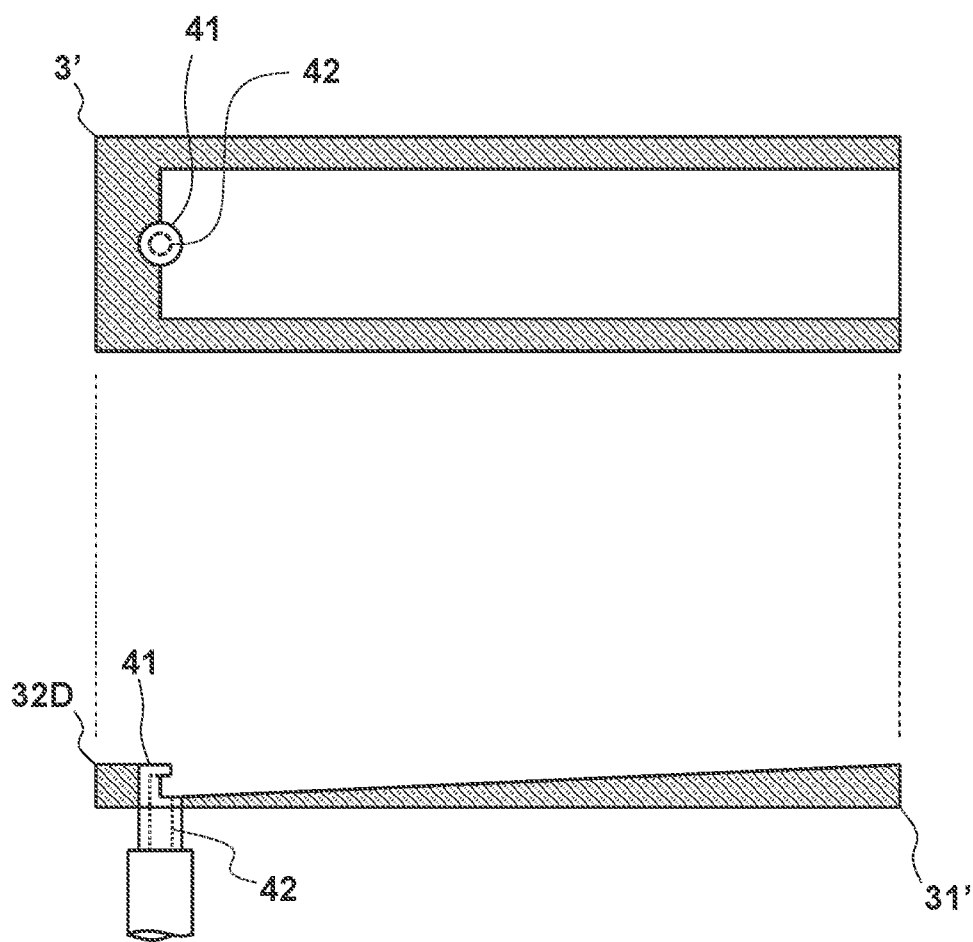
FIG. 5B shows a schematic top view and a schematic sectional view for explaining a step of a sample producing method.

FIG. 5B shows a top view and a sectional view showing a state in which the suction nozzle 41 is installed in the base plate 3'. Here, the suction nozzle 41, which is in a posture almost perpendicular to the base plate 3' in the horizontal posture, is inserted and fixed in the hole 311. However, the suction nozzle 41 may be fixed in a posture almost perpendicular to the tilting upper surface of the support portion 31'.

Figure 5C:
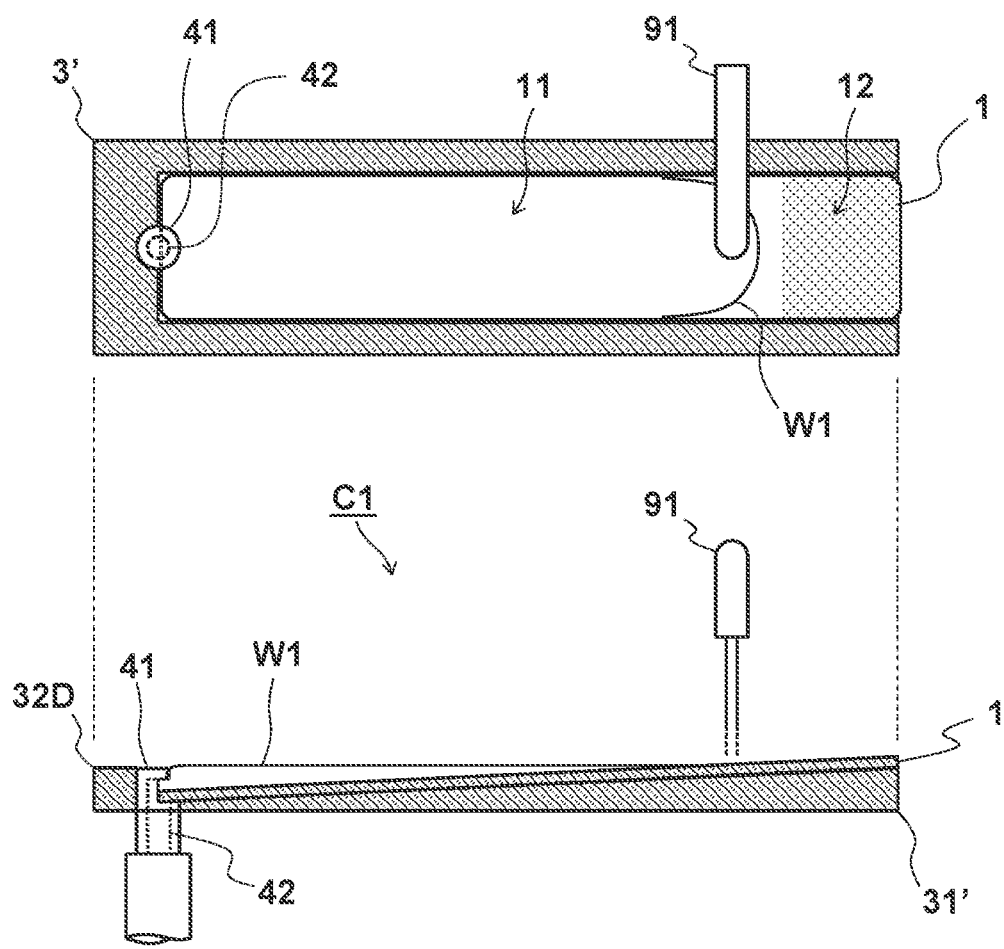
FIG. 5C shows a schematic top view and a schematic sectional view for explaining a step of the sample producing method.

FIG. 5C shows a top view and a sectional view showing a state in which the plate 1 is arranged on the base plate 3' in which the suction nozzle 41 is installed. According to the base plate 3', since the upper surface of the support portion 31' is a tilting surface provided at a predetermined angle (tilt angle θ3) in advance in the horizontal posture, the plate 1 is arranged in a tilt posture C1. For this reason, if the base plate 3' is used in place of the base plate 3 according to the first embodiment, when supplying the liquid onto the plate 1 by the liquid supply unit 91, the liquid pool W1 can be formed on the plate 1 such that the liquid depth on the side of the suction nozzle 41 becomes deeper in a state in which the base plate 3' is not tilted (not set in the tilt posture A1), and only the plate 1 is tilted in the tilt posture D1. That is, it can be said that if the base plate 3' is used, the operation of moving the base plate 3 to the tilt posture A1 in the step shown in FIG. 2C can be omitted.

Figure 6A:
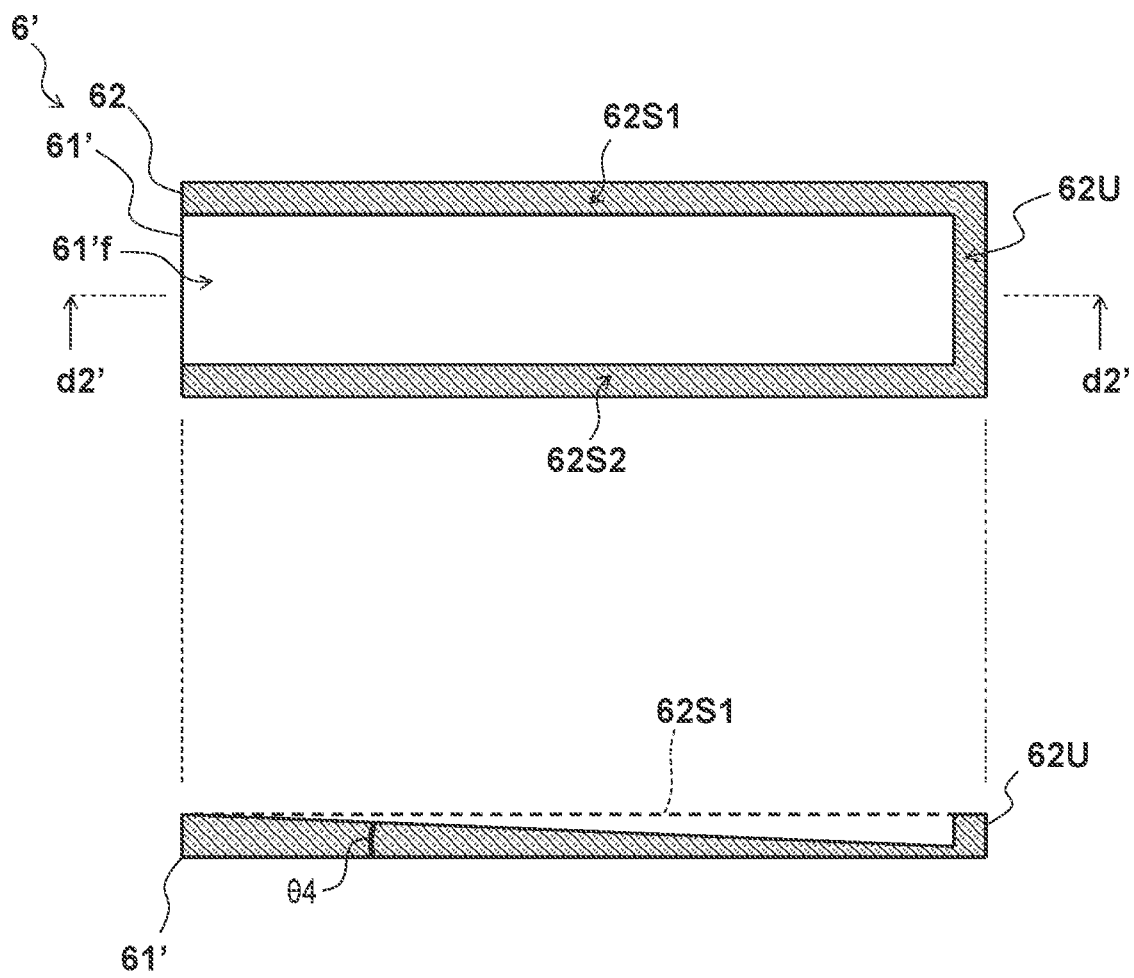
FIG. 6A shows a schematic top view and a schematic sectional view of the configuration of a base plate.

FIG. 6A shows a top view of a base plate 6' as another example of the base plate usable in the sample producing method according to the second embodiment and a sectional view taken along a line d2'-d2' in the top view. The base plate 6' is different from the base plate 6 (see FIG. 4A and the like) according to the second embodiment in that, in place of the support portion 61, the base plate 6' includes a support portion 61' whose upper surface is a tilting surface provided at a predetermined tilt angle in advance in the horizontal posture. That is, the base plate 6' is provided such that the support portion 61' gradually becomes thicker (the thickness of the support portion 61' increases) from one end portion on the side of the edge portion 62U to the other end portion on the opposite side (the opposite side of the one end portion with respect to a placement surface 61'f). A tilt angle θ4 of the upper surface of the support portion 61' can be about 1 degree. Note that the frame portion 62 is the same as in the base plate 6 (see FIG. 4A and the like).

Figure 6B:
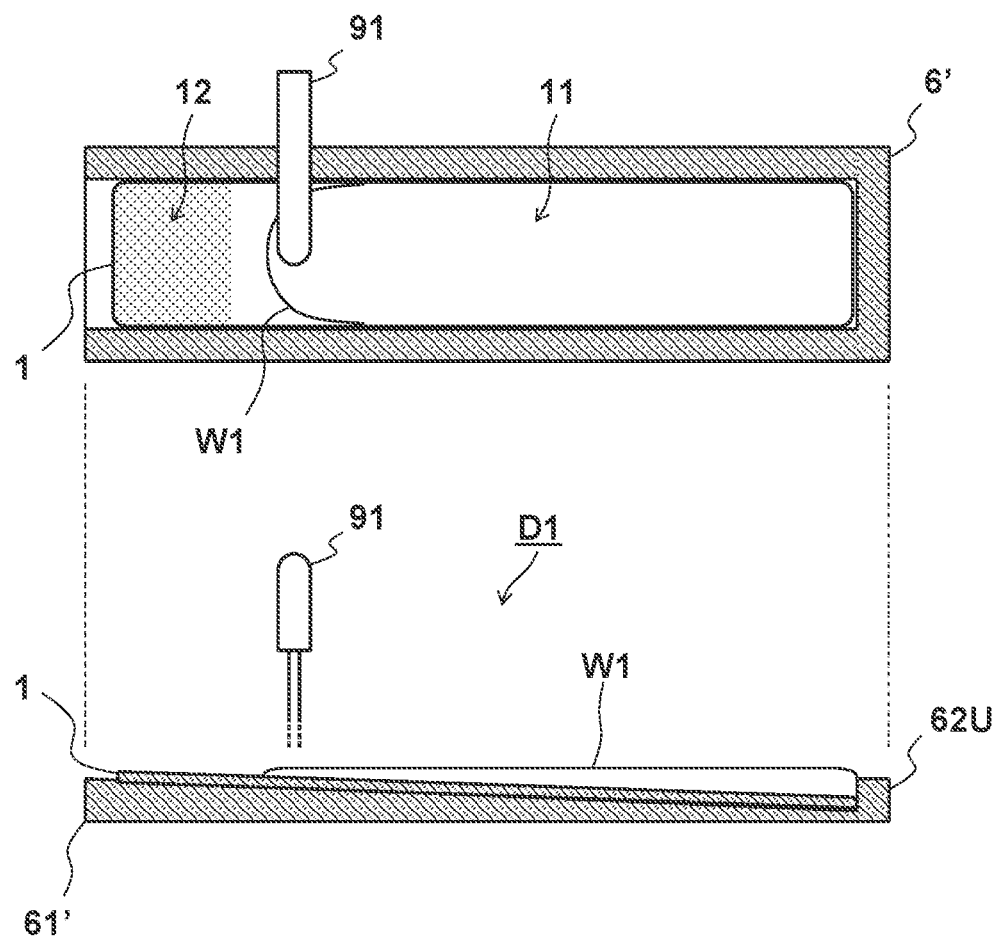
FIG. 6B shows a schematic top view and a schematic sectional view for explaining a step of a sample producing method.

FIG. 6B shows a top view and a sectional view showing a state in which the plate 1 is around on the base plate 6'. According to the base plate 6', since the upper surface of the support portion 61' is a tilting surface provided at a predetermined angle (tilt angle θ4) in advance in the horizontal posture, the plate 1 is arranged in a tilt posture D1. For this reason, if the base plate 6' is used in place of the base plate 6 according to the second embodiment, when supplying the liquid onto the plate 1 by the liquid supply unit 91, the liquid pool W1 can be formed on the plate 1 such that the liquid depth on the side of the edge portion 62U becomes deeper in a state in which the base plate 6' is not tilted (not set in the tilt posture B1), and only the plate 1 is tilted in the tilt posture D1. That is, it can be said that if the base plate 6' is used, the operation of moving the base plate to the tilt posture B1 in the step shown in FIG. 4C can be omitted.

In the above description, to facilitate understanding, the elements have names associated with their functional aspects. However, the elements are not limited to those having the contents described in the embodiments as main functions, and may have the functions auxiliary.

As described above, one aspect of the present invention is related to a sample producing method, and the sample producing method is a sample producing method of producing an observation sample (for example, SP) by placing an observation target object (for example, 2) on an optically transparent plate (for example, 1), comprising a placement step (for example, steps in FIG. 2D, 4D) of placing the observation target object on a surface of a liquid pool (for example, W1) retained on the plate, and a fixing step (for example, steps in FIG. 2E, 2F, 4E, 4F) of making an amount of a liquid of the liquid pool on the plate larger on one end portion (for example, P1) side of the plate than on the other end portion (for example, P2) side and attaching and fixing the observation target object to a surface of the plate sequentially from the other end portion toward the one end portion. Accordingly, after the observation target object is brought into contact with the plate surface on the liquid discharge upstream side, the observation target object contacts the plate surface sequentially from the liquid discharge upstream side to the liquid discharge downstream side. As a result, the observation target object can be fixed to the plate without causing wrinkles or twists in the observation target object. That is, the observation sample can appropriately be produced.

The invention is not limited to the foregoing embodiments, and various variations/changes are possible within the spirit of the invention.

REFERENCE SIGNS LIST

1 . . . plate, 2 . . . observation target object, SP . . . observation sample, W1 . . . liquid pool, P1 . . . one end portion (liquid discharge downstream-side end portion), P2 . . . other end portion (liquid discharge upstream-side end portion)

The invention claimed is:

1. A sample producing method of producing an observation sample by placing an observation target object on an optically transparent plate, comprising:
    an arranging step of arranging the optically transparent plate on a base plate;
    a placement step of placing the observation target object on a surface of a liquid pool retained on the optically transparent plate; and
    a fixing step of making an amount of a liquid of the liquid pool on the optically transparent plate larger on one end portion side of the optically transparent plate than on the other end portion side, and attaching and fixing the observation target object to a surface of the optically transparent plate sequentially from the other end portion toward the one end portion, wherein
    the base plate includes a first lyophobic portion at a peripheral edge portion of a portion where the optically transparent plate is arranged,
    in the arranging step, the optically transparent plate is arranged to be adjacent to the first lyophobic portion, and
    in the fixing step, a movement of the liquid of the liquid pool on the optically transparent plate toward the one end portion side is regulated by the first lyophobic portion, and the liquid of the liquid pool is discharged from the one end portion side so as to lower a liquid height level, such that a liquid depth of the liquid of the liquid pool becomes shallower on the other end portion side of the optically transparent plate than on the one end portion side.

2. The sample producing method according to claim 1, wherein, in the fixing step, the optically transparent plate is tilted to discharge the liquid of the liquid pool from the one end portion side of the optically transparent plate.

3. The sample producing method according to claim 2, wherein, in the fixing step, the optically transparent plate is tilted in a predetermined direction using a line parallel to the surface of the optically transparent plate as an axis.

4. The sample producing method according to claim 2, wherein
    the optically transparent plate has a rectangular shape including a first side and a second side, which cross each other, and
    in the fixing step, the optically transparent plate is tilted using a line parallel to one of the first side and the second side as the axis.

5. The sample producing method according to claim 1, wherein the base plate includes a liquid discharge mechanism, and, in the fixing step, the liquid of the liquid pool on the optically transparent plate is guided to the liquid discharge mechanism.

6. The sample producing method according to claim 5, wherein,
    in the arranging step, a lyophobic plate member including a second lyophobic portion on at least an edge portion is arranged on the base plate, and the optically transparent plate is arranged on the base plate, and
    in the fixing step, the liquid is discharged while regulating a movement of the liquid to the one end portion side by the second lyophobic portion.

7. The sample producing method according to claim 1, wherein, in the fixing step, the optically transparent plate is tilted in a predetermined direction such that the liquid depth of the liquid of the liquid pool on the optically transparent plate becomes deeper on the other end portion side of the optically transparent plate than on the one end portion side, and then, the optically transparent plate is tilted in a direction opposite to the predetermined direction such that the liquid depth of the liquid becomes deeper on the one end portion side than on the other end portion side, thereby discharging the liquid.

8. The sample producing method according to claim 1, further comprising a step of forming the liquid pool by supplying the liquid to a predetermined region on the optically transparent plate.

9. A sample producing method of producing an observation sample by placing an observation target object on an optically transparent plate, comprising:
    an arranging step of arranging the optically transparent plate on a base plate;
    a placement step of placing the observation target object on a surface of a liquid pool retained on the optically transparent plate; and
    a fixing step of making an amount of a liquid of the liquid pool on the optically transparent plate larger on one end portion side of the optically transparent plate than on the other end portion side, and attaching and fixing the observation target object to a surface of the optically transparent plate sequentially from the other end portion toward the one end portion, wherein
    the base plate includes a first lyophobic portion at a peripheral edge portion of a portion where the optically transparent plate is arranged,
    in the arranging step, the optically transparent plate is arranged to be adjacent to the first lyophobic portion, and
    in the fixing step, a movement of the liquid of the liquid pool on the optically transparent plate toward the one end portion side is regulated by the first lyophobic portion, and the liquid of the liquid pool is discharged from the one end portion side so as to lower a liquid height level, such that a liquid depth of the liquid of the liquid pool becomes shallower on the other end portion side of the optically transparent plate than on the one end portion side,
    the base plate includes a liquid discharge mechanism, and, in the fixing step, the liquid of the liquid pool on the optically transparent plate is guided to the liquid discharge mechanism,
    in the arranging step, a lyophobic plate member including a second lyophobic portion on at least an edge portion is arranged on the base plate, and the optically transparent plate is arranged on the base plate,
    in the fixing step, the liquid is discharged while regulating a movement of the liquid to the one end portion side by the second lyophobic portion, and
    in the arranging step, the lyophobic plate member including the second lyophobic portion on the one end portion of the optically transparent plate and a side edge portion different from the one end portion and the other end portion of the optically transparent plate is arranged on the base plate.

* * * * *

UNITED STATES PATENT AND TRADEMARK OFFICE
CERTIFICATE OF CORRECTION

| | |
|---|---|
| PATENT NO. | : 12,013,319 B2 |
| APPLICATION NO. | : 17/358444 |
| DATED | : June 18, 2024 |
| INVENTOR(S) | : Seigo Murakami |

It is certified that error appears in the above-identified patent and that said Letters Patent is hereby corrected as shown below:

In the Specification

Column 3, Line 46, delete "31$f$" and insert -- 31$f$. --.

Column 4, Line 8, delete "Ow" and insert -- $\theta$w --.

Column 4, Line 10, delete "<Ow," and insert -- <$\theta$w, --.

Column 4, Line 10, delete "<Ow," and insert -- <$\theta$w, --.

Column 11, Line 13, delete "61$f$" and insert -- 61$f$. --.

Signed and Sealed this
Seventeenth Day of September, 2024

Katherine Kelly Vidal
*Director of the United States Patent and Trademark Office*